(12) United States Patent
Yamazaki et al.

(10) Patent No.: US 12,716,045 B2
(45) Date of Patent: Aug. 25, 2026

(54) SAMPLING METHOD

(71) Applicant: Terumo Kabushiki Kaisha, Tokyo (JP)

(72) Inventors: Nozomu Yamazaki, Kanagawa (JP); Masatsugu Igarashi, Kanagawa (JP)

(73) Assignee: Terumo Kabushiki Kaisha (JP)

( * ) Notice: Subject to any disclaimer, the term of this patent is extended or adjusted under 35 U.S.C. 154(b) by 606 days.

(21) Appl. No.: 18/211,859

(22) Filed: Jun. 20, 2023

(65) Prior Publication Data

US 2023/0332086 A1 Oct. 19, 2023

Related U.S. Application Data

(63) Continuation of application No. PCT/JP2022/008733, filed on Mar. 2, 2022.

(30) Foreign Application Priority Data

Mar. 3, 2021 (JP) ................................ 2021-033649

(51) Int. Cl.

*C12M 3/00* (2006.01)
*B01L 3/00* (2006.01)
*C12M 1/00* (2006.01)
*C12M 1/26* (2006.01)
*C12M 1/34* (2006.01)

(52) U.S. Cl.

CPC ............ *C12M 33/04* (2013.01); *C12M 33/14* (2013.01); *C12M 39/00* (2013.01); *C12M 41/30* (2013.01); *C12M 41/40* (2013.01)

(58) Field of Classification Search

CPC ....... C12M 39/00; C12M 33/14; C12M 33/00
See application file for complete search history.

(56) References Cited

U.S. PATENT DOCUMENTS 4,952,127 A * 8/1990 Schmeisser ............. C12N 1/02 494/36
9,442,047 B2 9/2016 Biksacky
(Continued)

FOREIGN PATENT DOCUMENTS

JP H03147778 A 6/1991
JP H05227943 A 9/1993
(Continued)

OTHER PUBLICATIONS

Office Action issued in corresponding Japanese Application No. 2023-503886, dated Nov. 11, 2025 (5 pgs).
(Continued)

*Primary Examiner* — Nathan A Bowers
(74) *Attorney, Agent, or Firm* — Harness, Dickey & Pierce, P.L.C.

(57) ABSTRACT

A sampling device includes a sampling channel, a detection unit and a sample introduction channel. A cell culturing device or the sample introduction channel includes an aseptic filter in a section before the sampling channel. A sampling method includes a sampling step for introducing the sample from the culturing device and detecting the sample by the detection unit and an adhering substance removal step for removing an adhering substance adhering to the aseptic filter by allowing a fluid to flow from the sampling channel to the sample introduction channel.

15 Claims, 17 Drawing Sheets

(56) References Cited

U.S. PATENT DOCUMENTS

| | | | | |
|---|---|---|---|---|
| 2007/0128087 | A1* | 6/2007 | Cannizzaro | C12M 33/04 422/50 |
| 2012/0071788 | A1* | 3/2012 | Kunnecke | A61B 5/14525 600/573 |
| 2014/0123775 | A1* | 5/2014 | Newbold | C12M 37/00 73/864 |
| 2019/0290822 | A1* | 9/2019 | Igarashi | A61M 1/362261 |

FOREIGN PATENT DOCUMENTS

| | | | |
|---|---|---|---|
| JP | H11276825 | A | 10/1999 |
| JP | 2006518462 | A | 8/2006 |
| JP | 2010081809 | A | 4/2010 |
| JP | 2018510166 | A | 4/2018 |

OTHER PUBLICATIONS

Written Opinion of the International Searching Authority issued in PCT/JP2022/08733 (in Japanese and English translation) mailed May 24, 2022 (9 pgs).

* cited by examiner 10
11
36b
36
12
34
36a
36c
36d
18A
18B
18C
18
24
22
26
12
92
32
148
91
96
98
60
118
100
16
90
22
22
14
20

10 (24)
CULTURE MEDIUM RESERVOIR
14
28
40
16
22
30
30b
42
42b
42a
30a
P
P
P
P
12
34
36
36a
36b
36c
36d
60
56
132
130
54
46
52
28
28
48
WASTE LIQUID UNIT
20
32
CONTROL CIRCUIT
30
30d
44b
44a
44
30c

10
CULTURING DEVICE
11
54
56
132
130
CLEANING SOLUTION STORAGE UNIT
70
STANDARD SOLUTION STORAGE UNIT
72
73
94b
94a
94
96
60
90
71
65
P
92
66
141
P
142
140
131
139
144
138
134
136
148
146
84
64
62
76
PH
O2
CO2
78a
78b
78c
78
112
111
110
116a
116b
116c
116
75
121
120
122
GLUCOSE
LACTIC ACID
82a
82b
82
83a
83b
80
94c
86
WASTE LIQUID STORAGE UNIT
74
CONTROLLER
68

10
: CLAMP OPENED
: CLAMP CLOSED
CLEANING SOLUTION STORAGE UNIT
STANDARD SOLUTION STORAGE UNIT
CULTURING DEVICE
CONTROLLER
WASTE LIQUID STORAGE UNIT
PH
O2
CO2
GLUCOSE
LACTIC ACID
P
P
70
72
60
66
94
94a
94b
73
96
90
71
65
92
134
84
64
62
112
76
111
110
78
78a
78b
78c
116a
116b
116c
116
75
121
120
122
82
82a
82b
83a
83b
80
94c
86
74
11
54
56
132
130
141
140
142
131
136
148
146
139
144
138
68

FIG 6

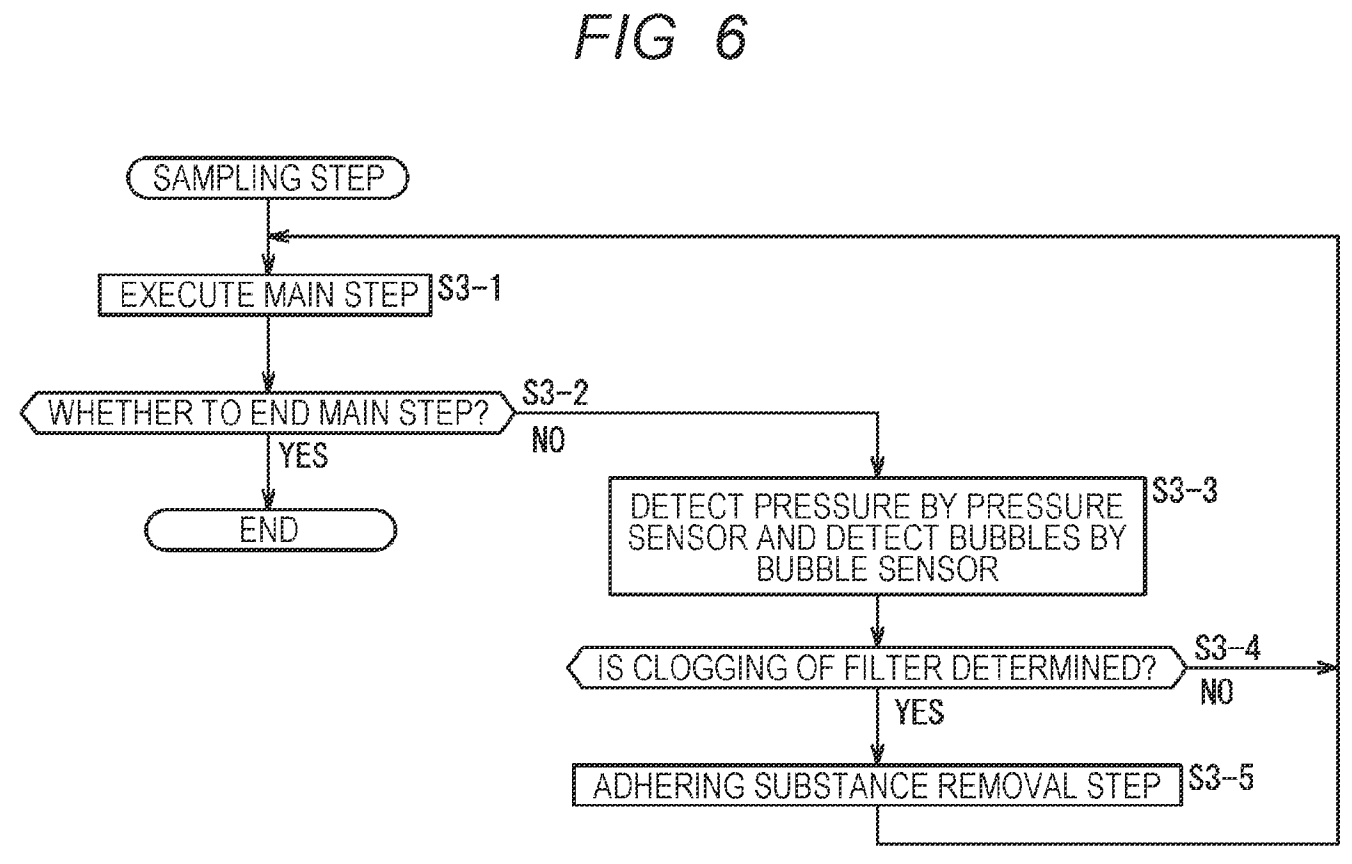

SAMPLING STEP

S3-1 EXECUTE MAIN STEP

S3-2 WHETHER TO END MAIN STEP?

YES

END

NO

S3-3 DETECT PRESSURE BY PRESSURE SENSOR AND DETECT BUBBLES BY BUBBLE SENSOR

S3-4 IS CLOGGING OF FILTER DETERMINED?

NO

YES

S3-5 ADHERING SUBSTANCE REMOVAL STEP

10
CLEANING SOLUTION STORAGE UNIT
STANDARD SOLUTION STORAGE UNIT
: CLAMP OPENED
: CLAMP CLOSED
CULTURING DEVICE
P
PH
O2
CO2
GLUCOSE
LACTIC ACID
WASTE LIQUID STORAGE UNIT
CONTROLLER

10
CULTURING DEVICE
CLEANING SOLUTION STORAGE UNIT
STANDARD SOLUTION STORAGE UNIT
WASTE LIQUID STORAGE UNIT
CONTROLLER
: CLAMP OPENED
: CLAMP CLOSED
PH
O2
CO2
GLUCOSE
LACTIC ACID
P
P
11
54
56
132
130
140
141
142
138
131
139
144
146
148
136
134
84
60
70
72
73
94
94a
94b
94c
96
90
71
65
92
66
62
64
76
112
111
110
116
116a
116b
116c
78
78a
78b
78c
75
121
120
122
83a
83b
80
82
82a
82b
86
74
68

10
CULTURING DEVICE
11
54
58
56
132
130
141
140
146
148
142
P
134
84
CLEANING SOLUTION STORAGE UNIT
70
STANDARD SOLUTION STORAGE UNIT
72
60A
96
94
94a
94b
73
71
65
90
66
92
P
64
62
76
112
111
110
PH
O2
CO2
116a
116b
116c
116
78a
78b
78c
78
75
121
120
122
GLUCOSE
LACTIC ACID
83a
83b
80
82a
82b
82
94c
WASTE LIQUID STORAGE UNIT
74
CONTROLLER
68

10
60A
70
CLEANING SOLUTION STORAGE UNIT
72
STANDARD SOLUTION STORAGE UNIT
66
: CLAMP OPENED
: CLAMP CLOSED
94
96
94a
73
94b
P
90
71
65
92
134
84
64
62
112
76
111
110
PH
O2
CO2
78a
78b
78c
78
116a
116b
116c
116
142
P
11
CULTURING DEVICE
54
58
56
132
130
141
148
140
146
75
121
120
122
GLUCOSE
LACTIC ACID
82a
82b
82
83a
83b
80
94c
68
CONTROLLER
WASTE LIQUID STORAGE UNIT
74

10
CULTURING DEVICE
11
54
58
56
132
130
141
140
146
148
142
P
134
84
CLEANING SOLUTION STORAGE UNIT
70
60B
STANDARD SOLUTION STORAGE UNIT
72
73
94b
94a
94
96
90
71
65
150
152
92
P
66
62
64
76
112
PH
O2
CO2
111
110
116a
116b
116c
116
78a
78b
78c
78
75
121
120
122
GLUCOSE
LACTIC ACID
83a
83b
80
82a
82b
82
94c
WASTE LIQUID STORAGE UNIT
74
CONTROLLER
68

10
60B
70
CLEANING SOLUTION STORAGE UNIT
72
STANDARD SOLUTION STORAGE UNIT
66
94
94a
73
94b
96
P
71
65
92
90
150
152
134
84
P
142
11
CULTURING DEVICE
54
58
56
132
130
141
148
140
146
68
CONTROLLER
: CLAMP OPENED
: CLAMP CLOSED
64
62
112
76
111
110
PH
O2
CO2
78a
78b
78c
78
116a
116b
116c
116
75
121
120
122
GLUCOSE
LACTIC ACID
82a
82b
82
83a
83b
80
94c
WASTE LIQUID STORAGE UNIT
74

10
60B
CLEANING SOLUTION STORAGE UNIT
STANDARD SOLUTION STORAGE UNIT
: CLAMP OPENED
: CLAMP CLOSED
CULTURING DEVICE
CONTROLLER
PH
O2
CO2
GLUCOSE
LACTIC ACID
WASTE LIQUID STORAGE UNIT
P
P
11
54
56
58
62
64
65
66
68
70
71
72
73
74
75
76
78
78a
78b
78c
80
82
82a
82b
83a
83b
84
90
92
94
94a
94b
94c
96
110
111
112
116
116a
116b
116c
120
121
122
130
132
134
140
141
142
146
148
150
152

10
60C
CLEANING SOLUTION STORAGE UNIT
70
STANDARD SOLUTION STORAGE UNIT
72
66
94
96
94a
94b
73
P
71
65
92
90
134
84
64
62
76
111
112
110
PH
O2
CO2
78a
78b
78c
78
116a
116b
116c
116
P
142
11
CULTURING DEVICE
54
58
56
132
130
141
148
140
146
75
121
120
122
GLUCOSE
LACTIC ACID
82a
82b
82
83a
83b
80
160
164
161
162
94c
WASTE LIQUID STORAGE UNIT
74
68
CONTROLLER

10
: CLAMP OPENED
: CLAMP CLOSED
PH
O2
CO2
GLUCOSE
LACTIC ACID
WASTE LIQUID STORAGE UNIT
STANDARD SOLUTION STORAGE UNIT
CLEANING SOLUTION STORAGE UNIT
CULTURING DEVICE
CONTROLLER
P
P
11
54
56
58
60C
62
64
65
66
68
70
71
72
73
74
75
76
78
78a
78b
78c
80
82
82a
82b
83a
83b
84
90
92
94
94a
94b
94c
96
110
111
112
116
116a
116b
116c
120
121
122
130
132
134
140
141
142
146
148
160
161
162
164

10
CULTURING DEVICE
11
54
58
56
132
130
141
140
146
148
142
134
84
CLEANING SOLUTION STORAGE UNIT
70
STANDARD SOLUTION STORAGE UNIT
72
60C
96
94
94a
94b
73
71
65
92
66
90
: CLAMP OPENED
: CLAMP CLOSED
62
64
76
112
111
110
PH
O2
CO2
116a
116b
116c
116
78a
78b
78c
78
75
121
120
122
GLUCOSE
LACTIC ACID
83a
83b
80
82a
82b
82
161
94c
162
160
164
AIR
WASTE LIQUID STORAGE UNIT
74
CONTROLLER
68

SAMPLING METHOD

CROSS-REFERENCE TO RELATED APPLICATIONS

The present application is a continuation application of the International Patent Application No. PCT/JP2022/008733 filed on Mar. 2, 2022, which designated the U.S. and claims the benefit of priority from Japanese Patent Application No. JP2021-033649 filed on Mar. 3, 2021. The entire disclosures of the above-identified applications are incorporated herein by reference.

FIELD

The present disclosure relates to a sampling method for collecting a liquid sample from a cell culturing device.

BACKGROUND

A sampling device for collecting a liquid sample from a culturing device includes a sampling channel and a pump that is configured to draw a sample (e.g., culture medium) from a sample introduction channel that connects the culturing device to the sampling channel. The sampling device may also include a detection unit. The detection unit can detect components contained in the sample and amounts (concentrations) of the components.

When this type of sampling device is used for collecting a sample from a culturing device, an aseptic filter is often installed in a sample outflow channel of the culturing device in order to prevent intrusion of bacteria into the culturing device from the sampling device. However, as the culture medium is periodically collected during the culturing process, aggregates of proteins and the like contained in the culture medium can be deposited on the aseptic filter gradually clogging the aseptic filter. Clogs in the aseptic filter can make it such that a specified amount of sample cannot be collected and/or the sample introduction channel to have a negative pressure. Negative pressure in the sample introduction channel can cause gas concentration changes, generating, for example, bubbles.

Accordingly, there is a need for a sampling method for using a sampling device that can reduce clogging of aseptic filters.

SUMMARY

In at least one example embodiment, the present disclosure provides a sampling method using a sampling unit to collect a liquid sample from a cell culturing unit t. The sampling unit may include a sampling channel through which the sample flows, a detection unit provided in the sampling channel so as to come in contact with the sample, and a sample introduction channel connecting the sampling channel and the culturing unit upstream of the detection unit. One of the culturing unit and the sample introduction channel includes an aseptic filter. The sampling method may include a sampling step and an adhering substance removal step. The sampling step may include introducing the sample from the culturing unit to the sampling channel through the sample introduction channel and detecting the sample using the detection unit. The adhering substance removal step may include removing an adhering or clogging substance adhered to the aseptic filter, for example, in the sampling step by allowing a fluid to flow from the sampling channel to the sample introduction channel.

BRIEF DESCRIPTION OF DRAWINGS

FIG. 6 is a flowchart further illustrating the sampling step as illustrated in FIG. 4 in accordance with at least one example embodiment of the present disclosure.

DETAILED DESCRIPTION

Example embodiments of the present disclosure will now be described in detail with reference to the drawings.

Figure 1:
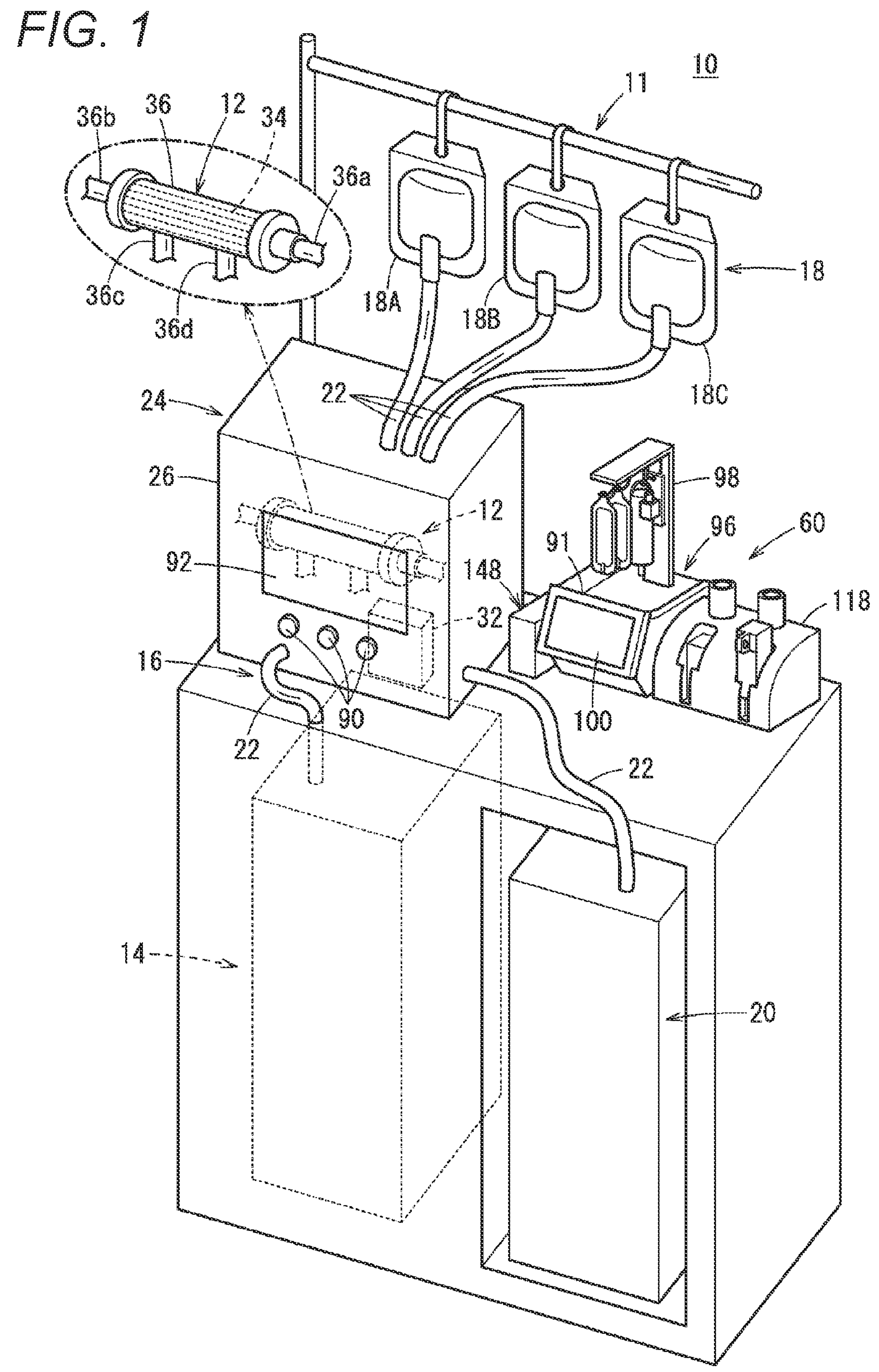
FIG. 1 is a perspective view a cell culturing system including a sampling device in accordance with at least one example embodiment of the present disclosure.

A cell culturing system 10 for culturing biological cells in regenerative medicine as illustrated in FIG. 1. An example sampling device 60 may be used with the cell culturing system 10. The sampling device 60 may be configured to sample a culture medium during culture of the cells by the cell culturing system 10 and measures the state of the culture medium. For example, the cell culturing system 10 may continue cell culture for a long period of time by discharging lactic acid, carbon dioxide, and/or the like (including, for example, unused medium and oxygen) as generated during cell culture from a reactor 12, which may be a cell culture vessel, while supplying a culture medium or oxygen to the reactor 12.

The biological cells are not particularly limited. In at least one example embodiment, the biological cells may include cells contained in blood (e.g., T cells and/or the like) and/or stem cells (e.g., ES cells, iPS cells, mesenchymal stem cells, and/or the like). Any appropriate culture medium may be selected for use with the selected biological cells. For example, the culture medium may include a basic solution that includes amino acids, vitamins, serum, and/or the like. The basic solution may include, for example, a balanced salt solution (BSS).

The cell culturing system 10 may include a culturing device 11 (also referred to as a culturing unit) in which a reactor 12 is set and cells are actually cultured and a sampling device 60 (also referred to as a sampling unit) that collects a liquid sample from the culturing device 11 during the culture. Although only one reactor 1 is illustrated in FIG. 1, it should be appreciated that in other embodiments the culturing device 11 may include a plurality of reactors 12. Although only one culturing device 11 is illustrated in FIG. 1, it should be appreciated that in other embodiments, the cell culturing system 10 may include a plurality of culturing devices 11 connected to one sampling device 60. Although the cell culturing system 10 as illustrated in FIG. 1 includes the culturing unit and the sampling unit as are separate units, components, parts, or pieces, it should be appreciated that in other embodiments, the culturing unit and the sampling unit may be provided as an integrated (unified) unit or component or part or piece.

The culturing device 11 may include a culture medium reservoir 14 configured to store a culture medium, a flow channel 16 provided between the reactor 12 and the culture medium reservoir 14, a plurality of medical bags 18 connected to the flow channel 16, and/or a waste liquid unit 20 configured to store a liquid discharged through the flow channel 16.

The culture medium reservoir 14 may include a hard tank that is configured to store a comparatively large amount of culture medium. The flow channel 16 may include multiple tubes 22. The multiple tubes 22 may be connected, respectively, to the reactor 12, the culture medium reservoir 14, the plurality of medical bags 18, and/or the waste liquid unit 20.

The plurality of medical bags 18 may include a cell solution bag 18A configured to store a liquid that includes cells (e.g., cell solution), a cleaning solution bag 18B configured to store a cleaning solution, a stripping solution bag 18C configured to store a stripping solution, and/or a collection bag (not illustrated) configured to collect cultured cells. The cleaning solution may include a liquid used at the time of priming of the reactor 12 and/or the flow channel 16. The cleaning solution may include a buffer solution and/or a physiological saline solution. The buffer solution may include, for example, phosphate buffer salts (PBS) and/or tris-buffered saline (TBS). The stripping solution may include a liquid for stripping the cells cultured by a culture treatment. For example, as the stripping solution may include trypsin and/or EDTA.

When the cell culturing system 10 is constructed, the flow channel 16 may be set so as to pass through a flow path control mechanism 24 of the culturing device 11. The flow path control mechanism 24 may include a housing 26 that is configured to house a part of the flow channel 16. The flow path control mechanism 24 may also include, in the housing 26, a clamp 28 that is configured to open and close a predetermined tube 22, a pump 30 that is configured to allow a liquid in the tube 22 to flow, and/or a control circuit 32 that is configured to control operations of the clamp 28 and/or the pump 30 (see FIG. 2).

The reactor 12 may be disposed in the housing 26 of the flow path control mechanism 24. The reactor 12 may include a plurality of hollow fibers 34 (e.g., 10,000 or more) and a case 36 that accommodates the plurality of hollow fibers 34. Each of the hollow fibers 34 may include a lumen (not illustrated), and cells may be seeded on an inner peripheral surface defining the lumen. Each of the hollow fibers 34 may include a plurality of pores (not illustrated) that allow communication between the outside of the hollow fibers and the lumen. For example, each pore may transmit a solution or a low-molecular-weight substance without transmitting cells or proteins. A culture medium or the like may be supplied to the cells seeded on the inner peripheral surface of the hollow fiber 34 through the lumen and/or the pores. The configuration in which the liquid mainly flows through the lumen of the hollow fiber 34 may be referred to as intra capillary (IC), and the configuration in which the liquid mainly flows through the outer side of the hollow fiber 34 may be referred to as extra capillary (EC).

Each of the cases 36 may include a first IC terminal **36*a* and/or a second IC terminal 36*b* that communicate with the lumens of the hollow fibers 34. Each of the cases 36 may also include a first EC terminal 36*c* and/or a second EC terminal 36*d* that communicate with a space outside the hollow fibers 34 in the case 36. The tube 22** may be connected to each terminal.

Figure 2:
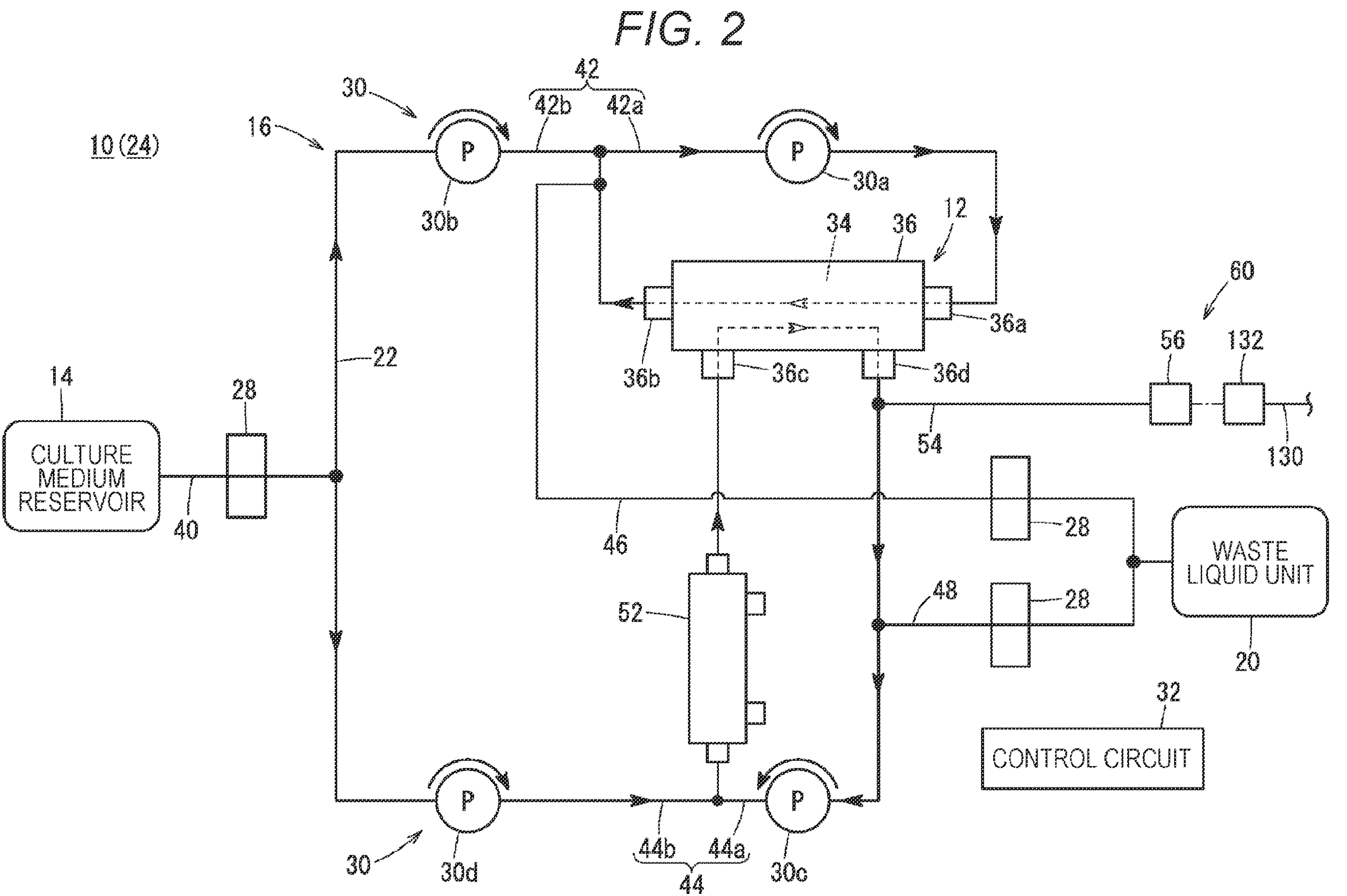
FIG. 2 is a schematic illustrating a channel for a culture medium in the cell culturing system as illustrated in FIG. 1 in accordance with at least one example embodiment of the present disclosure.

As illustrated in FIG. 2, the flow channel 16 may include a medium delivery route 40 that is connected to the culture medium reservoir 14 and an IC route 42 (internal route) and an EC route 44 (external route) that are branched from the medium delivery route 40. The IC route 42 may include a channel for supplying a liquid to the lumen of the hollow fibers 34. The EC route 44 may include a path for supplying liquid into the case 36 outside the hollow fibers 34.

The IC route 42 may include an IC circulation circuit **42*a* capable of circulating liquid with the reactor 12 and/or an IC supply circuit 42*b* through which liquid can flow from the culture medium delivery route 40 to the IC circulation circuit 42*a*. The IC circulation circuit 42*a* may be connected to the first IC terminal 36*a* and the second IC terminal 36*b* of the reactor 12** and may include an IC circulation pump 30*a* that allows liquid to flow through the lumen of the hollow fibers 34. An IC waste liquid circuit 46 that discharges a culture medium to the waste liquid unit 20 may be connected to the IC circulation circuit 42*a* on the downstream side of the reactor 12. The IC supply circuit 42*b* may include an IC supply pump 30*b* configured to allow liquid to flow from the culture medium delivery route 40 to the IC circulation circuit 42*a*.

The EC route 44 may include an EC circulation circuit 44*a* capable of circulating liquid with the reactor 12 and/or an EC supply circuit 44*b* through which liquid can flow from the culture medium delivery route 40 to the EC circulation circuit 44*a*. The EC circulation circuit 44*a* may be connected to the first EC terminal 36*c* and the second EC terminal 36*d* of the reactor 12 and may include an EC circulation pump 30*c* that circulates liquid on the outside of the hollow fibers 34. A gas exchanger 52 may be provided upstream of the reactor 12 in the EC circulation circuit 44*a*. The gas exchanger 52 may be configured to discharge carbon dioxide mixed in the culture medium and to mix a predetermined gas component (for example, nitrogen $N_2$: 75%, oxygen $O_2$: 20%, and/or carbon dioxide $COd_2$: 5%) with the culture medium. An EC waste liquid circuit 48 that discharges a culture medium to the waste liquid unit 20 may be connected to the EC circulation circuit 44*a* downstream of the reactor 12. The EC supply circuit 44*b* may be provided with an EC supply pump 30*d* for allowing liquid to flow from the culture medium delivery route 40 to the EC circulation circuit 44*a*.

A plurality of medical bags 18 (e.g., cell solution bag 18A, cleaning solution bag 18B, and/or stripping solution bag 18C) may be connected to the IC supply circuit 42*b* upstream of the IC supply pump 30*b* or the EC supply circuit 44*b* upstream of the EC supply pump 30*d* via a plurality of tubes 22 in addition to the culture medium reservoir 14. It should be appreciated that in certain embodiments, the medical bags 18 may be replaced with a collection bag and/or the like using a sterile connecting device that sterilizes and bonds the bag depending on the intended use.

The sampling device 60 may be connected to the EC circulation circuit 44*a* of the culturing device 11 at a position (between the reactor 12 and the EC waste liquid circuit 48) near the downstream side (second EC terminal 36*d*) of the reactor 12. One end of a sample outflow channel 54 through which a culture medium as a liquid sample flows out may be connected to the EC circulation circuit 44*a*. A culturing-device-side connector 56 may be provided at the other end of the sample outflow channel 54. The culturing-device-side connector 56 may be mutually connectable to a sampling-device-side connector 132 of the sampling device 60. In at least one example embodiment, the sample outflow channel 54 may be connected to the IC circulation circuit 42*a* on the downstream side (second IC terminal 36*b*) of the reactor 12.

Figure 3:
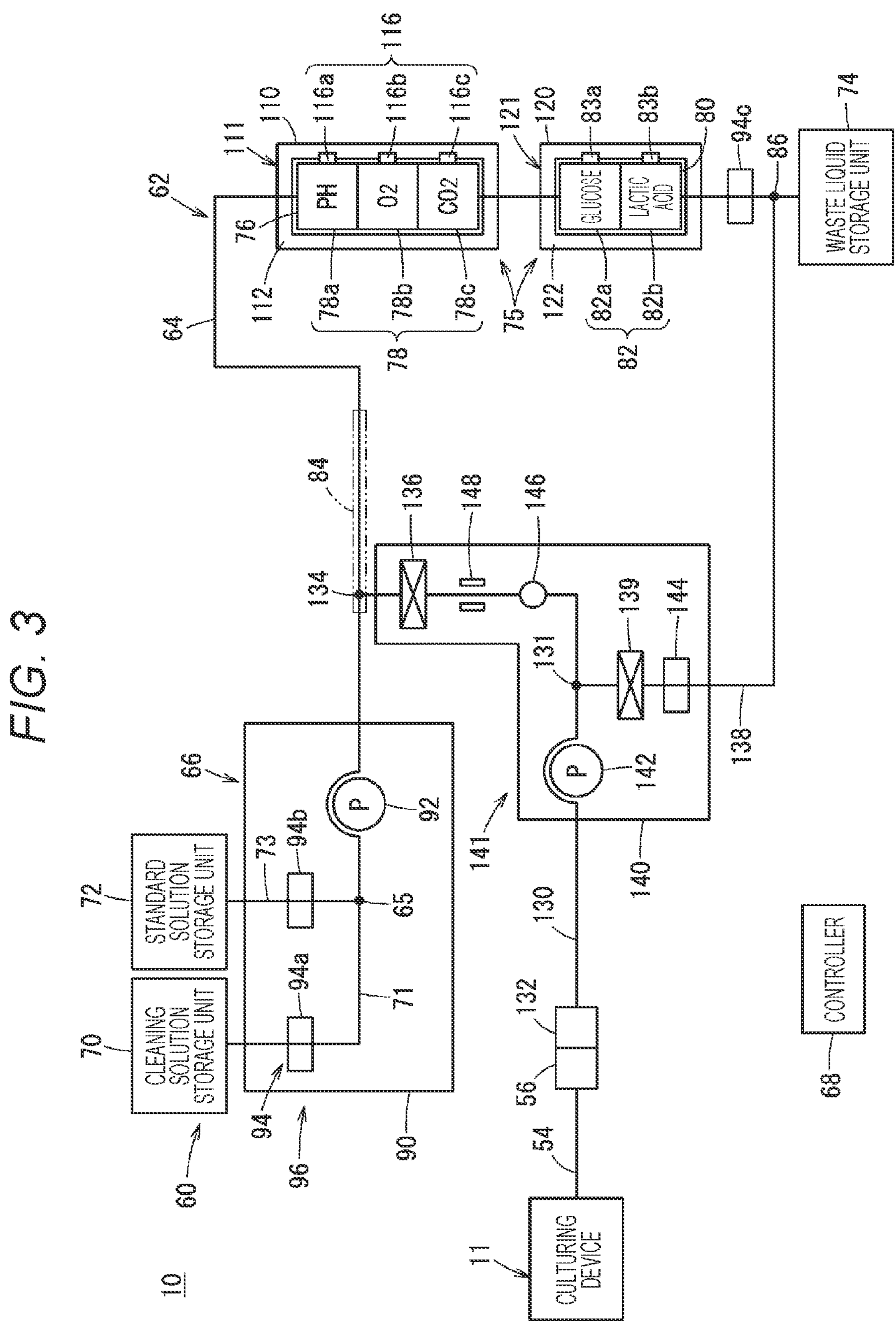
FIG. 3 is a schematic illustrating an example channel of the sampling device as illustrated in FIG. 1 in accordance with at least one example embodiment of the present disclosure.

The sampling device 60 is illustrated in FIG. 3. The sampling device 60 may be configured to collect a sample of a culture medium from one or more culturing devices 11 and to detect components contained in the sample and amounts (concentrations) of the components. The sampling device 60 may include a sampling kit 62 having a sampling channel 64 through which a sample is collected, a plurality of mechanisms 66 in which the sampling kit 62 may be detachably set and/or a controller 68 that is configured to control operations of the plurality of mechanisms 66. In at least one example embodiment, the sampling kit 62 may be disposable product and the plurality of mechanisms 66 may be a reusable product.

In addition to the sampling channel 64, the sampling kit 62 may include a cleaning solution storage unit 70, a standard solution storage unit 72, a waste liquid storage unit 74, and/or a detection unit 75 (including, for example, a first detection unit 76 and a second detection unit 80). The sampling channel 64 may include a flexible tube having an appropriate thickness by which the sample can pass therethrough. The cleaning solution storage unit 70 may be connected to a branch point 65 to which one end of the sampling channel 64 may be connected, for example, via a cleaning solution branch path 71. The standard solution storage unit 72 may also be connected to the branch point 65 via a standard solution branch path 73. The other end of the sampling channel 64 may be connected to the waste liquid storage unit 74.

The cleaning solution storage unit 70 and/or the standard solution storage unit 72 may include a soft resin material that is formed into a bag shape (medical bag). The soft resin material may include, for example, polyvinyl chloride and/or polyolefin. The cleaning solution storage unit 70 and the standard solution storage unit 72 are not particularly limited as long as the storage units are configured to store liquid. The waste liquid storage unit 74 may share a tank with the waste liquid unit 20 of the culturing device 11, but it is not limited thereto, and a medical bag or the like may be applied.

The cleaning solution storage unit 70 may be configured to store a cleaning solution. The cleaning solution is not particularly limited and may include, for example, a buffer solution, a physiological saline solution, and/or the like, such as described in the instance of the cleaning solution bag 18B.

The standard solution storage unit 72 may be configured to store a standard solution. The standard solution may include a liquid for calibrating the first detection unit 76 and/or the second detection unit 80. The standard solution may have a pH value, a glucose value (glucose concentration), and/or a lactic acid value (lactic acid concentration) set to prescribed values.

The first detection unit 76 and the second detection unit 80 may be provided in series and separated from each other at an intermediate position of the sampling channel 64. It should be appreciated that although the detection unit 75 as illustrated includes the first detection unit 76 and the second detection unit 80, in other embodiments the detection unit 75 may have a structure in which the first detection unit 76 and the second detection unit 80 are integrated, and still other embodiments where the first detection unit 76 and the second detection unit 80 are divided into three or more units.

The first detection unit 76 may include a tubular member having multiple first elements 78 that come in contact with (in liquid contact with) the sample in a flow path in the sampling channel 64. The multiple first elements 78 may include, for example, a pH chip 78*a* for measuring the pH in the sample, an $O_2$ chip 78*b* for measuring the 02 concentration in the sample, and/or a $CO_2$ chip 78*c* for measuring the $CO_2$ concentration in the sample. The pH chip 78*a* may be colored by reaction with $H^+$ and $OH^-$. The $O_2$ chip 78*b* may be colored by reaction with $O_2$. The $CO_2$ chip 78*c* may be colored by reaction with $CO_2$.

The second detection unit 80 may include a tubular member having multiple second elements 82 that come in contact with (in liquid contact with) the sample in the flow path in the sampling channel 64 and is provided downstream (waste liquid storage unit 74 side) of the first detection unit 76. For example, the multiple second elements 82 may include biosensors that react an enzyme with a circulating sample and detect a current change or the like. The multiple second elements 82 may include, for example, a glucose chip 82*a* that measures the glucose concentration in the sample and/or a lactic acid chip 82*b* that measures the lactic acid concentration in the sample. The glucose chip 82*a* may be electrically connected to a glucose terminal 83*a* protruding to the outside of the tubular member. The lactic acid chip 82*b* may be electrically connected to a lactic acid terminal 83*b* protruding to the outside of the tubular member.

In addition, the sampling kit 62 may include a connection part 84 to which one or more sample introduction channels 130 can be connected between the branch point 65 of the sampling channel 64 and the first detection unit 76. The connection part 84 may include, for example, a member obtained by integrally molding a plurality of branch ports each having a valve (not illustrated) that closes when the sample introduction channel 130 is not attached and opens as the sample introduction channel 130 is attached (in FIG. 3, the connection part 84 is indicated as a range surrounded by a two-dot chain line for convenience). Alternatively, a port to which the sample introduction channel 130 can be connected with the sampling channel 64 being kept aseptic can be applied to the connection part 84.

A part of the sampling kit 62 may be set in a main mechanism 90 which may be one of the plurality of mechanisms 66 as illustrated in FIG. 3. The main mechanism 90 may also include, in the housing 91 (see FIG. 1), a main-mechanism-side pump 92 and a plurality of clamps 94 that are configured to open and close flow paths in the respective channels (tubes). Although not illustrated, it should be appreciated that in at least one example embodiment, the controller 68 that controls the sampling device 60 may be also provided in the main mechanism 90. The sampling kit 62 may be set in the main mechanism 90, by which a main unit 96 of the sampling device 60 may be constructed.

The sampling channel 64 extending between the branch point 65 and the connection part 84 may be disposed in the main-mechanism-side pump 92. The main-mechanism-side pump 92 may have a circular wound portion around which the sampling channel 64 can be wound so as to wrap around and may be configured to rotate so as to apply a peristaltic action on the wrapping sampling channel 64 (tube) thereby allowing an internal fluid (liquid, air, etc.) to flow.

The multiple clamps 94 may include a cleaning solution clamp 94*a* configured to open and close the cleaning solution branch path 71, a standard solution clamp 94*b* configured to open and close the standard solution branch path 73, and/or a waste liquid clamp 94*c* configured to open and close the sampling channel 64 between the second detection unit 80 and the waste liquid storage unit 74.

The first detection unit 76 of the sampling kit 62 may be set in a first measuring instrument 110 which may be one of the plurality of mechanisms 66, whereby a first sensor unit 111 is constructed. The first measuring instrument 110 may include a holder 112 that accommodates the first detection unit 76 and a measurement body 116 fixed to the holder 112 and configured to optically measure the plurality of first elements 78.

The measurement body 116 may be provided with a pH detector 116*a*, an 02 detector 116*b*, and/or a $CO_2$ detector 116*c* that are arranged to respectively face the pH chip 78*a*, the $O_2$ chip 78*b*, and/or the $CO_2$ chip 78*c* with the first detection unit 76 being held by the holder 112. Under the control of the controller 68, the measurement body 116 may be configured to emit measurement light having a wavelength corresponding to the characteristics of each of the first elements 78, to receive excitation light generated from the first element 78 by excitation, and to transmit a detection signal thereof to the controller 68. The measurement body 116 may be set in the calibration device 118 (see FIG. 1) as installed at a position adjacent to the main mechanism 90 by the user, such that calibration may be performed.

The second detection unit 80 of the sampling kit 62 may be set in a second measuring instrument 120, which may be one of the plurality of mechanisms 66, whereby a second sensor unit 121 is constructed. The second measuring instrument 120 may include a case 122 that can accommodate the second detection unit 80 and an enzyme detector (not illustrated) that may be electrically connected to the glucose terminal 83*a* and/or the lactic acid terminal 83*b*. The enzyme detector may be configured to detect a current value from each of the glucose chip 82*a* and/or the lactic acid chip 82*b* and to transmit a detection signal based on the current value to the controller 68.

In order to introduce a sample to be measured by the first sensor unit 111 and the second sensor unit 121, the sample introduction channel 130 may be connected to the connection part 84 of the sampling kit 62 (sampling channel 64). Similar to the sampling channel 64, the sample introduction channel 130 may include a flexible tube having an appropriate thickness by which the sample can pass therethrough.

The sample introduction channel 130 may have, at one end, the sampling-device-side connector 132 configured to be connected to the culturing-device-side connector 56 (see also FIG. 2). A plug (not illustrated) attachable to and detachable from the connection part 84 may be provided at the other end of the sample introduction channel 130. A portion where the plug of the sample introduction channel 130 is connected to the sampling channel 64 may be referred to as a connection point 134. The sampling channel 64 and the sample introduction channel 130 may be inseparably connected to each other at the connection part 84.

An aseptic filter 136 may be provided in the sample introduction channel 130 between the sampling-device-side connector 132 and the plug (connection point 134). The aseptic filter 136 may be configured to maintain an aseptic state of the sample introduction channel 130 and the culturing device 11 upstream of the aseptic filter 136.

Figure 8A:
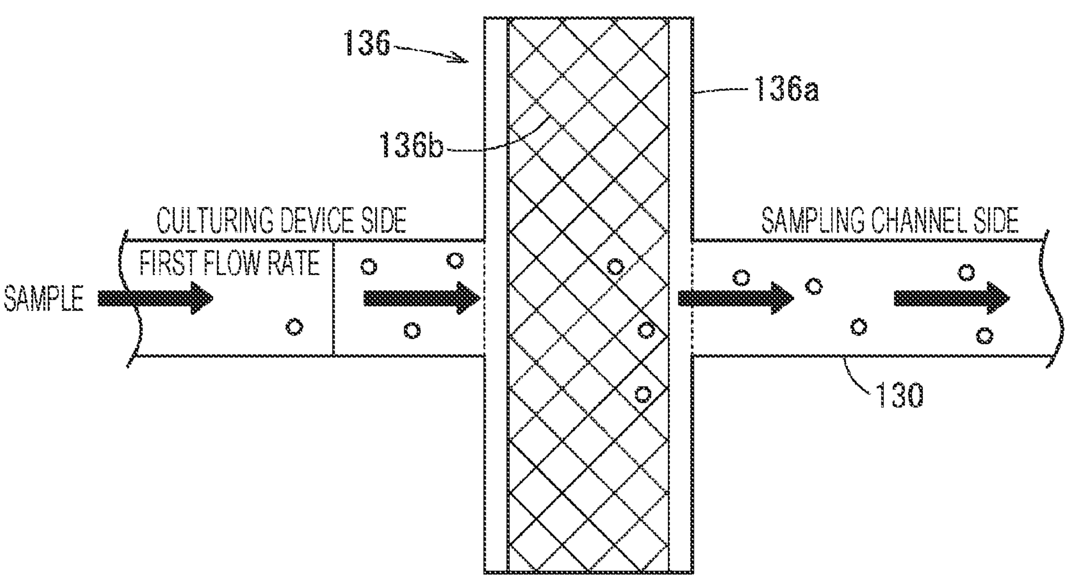
FIG. 8A is a schematic illustrating movement of aggregates with respect to an aseptic filter in a first stage of the main step as illustrated in FIG. 6 in accordance with at least one example embodiment of the present disclosure.

For example, the aseptic filter 136 may include a housing 136*a* connected to the sample introduction channel 130 and a mesh body 136*b* accommodated in a space in the housing and in communication with the flow path of the sample introduction channel 130 (see FIG. 8A). A membrane filter or a depth filter having an appropriate size capable of capturing bacteria or the like may be applied to the mesh body 136*b*.

A waste liquid channel 138 may be connected to the sample introduction channel 130 upstream of the aseptic filter 136. The waste liquid channel 138 may connect a branch point 131 of the sample introduction channel 130 provided between the aseptic filter 136 and the sampling-device-side connector 132 and a branch point 86 on the downstream side of the second detection unit 80 (waste liquid clamp 94*c*) of the sampling channel 64. The cleaning solution guided to the sample introduction channel 130 may be supplied to the waste liquid storage unit 74 through the waste liquid channel 138.

The waste liquid channel 138 may include an aseptic filter 139 at a position near the branch point 131 (near the sample introduction channel 130). The aseptic filter 139 may include a filter similar to the aseptic filter 136. The aseptic filter 139 maintains an aseptic state of the culturing device 11.

A part of the sample introduction channel 130 may be detachably set to an introduction mechanism 140 which is one of the plurality of mechanisms 66. The introduction mechanism 140 may include an introduction pump 142 and a waste liquid channel clamp 144. The introduction mechanism 140 may also include a pressure sensor 146 that is configured to detect the pressure in the flow path of the sample introduction channel 130 and/or a bubble sensor 148 that is configured to detect bubbles in the flow path of the sample introduction channel 130. The sample introduction channel 130 may be set in the introduction mechanism 140, by which an introduction unit 141 of the sampling device 60 is constructed.

The introduction unit 141 may be configured such that a part of the sample introduction channel 130, the introduction pump 142, the pressure sensor 146, and/pr the bubble sensor 148 can be integrally handled. The sample introduction channel 130 may extend from the introduction unit 141 and may be connected to the connection part 84 on the main unit 96.

The introduction pump 142 may be disposed upstream of the branch point 131 in the sample introduction channel 130 (between the branch point 131 and the sampling-device-side connector 132). The introduction pump 142 may include a circular wound portion around which the sample introduction channel 130 can be wound so as to wrap around and may rotate so as to apply a peristaltic action on the wrapping sample introduction channel 130 (tube), thereby allowing an internal fluid to flow.

The waste liquid channel clamp 144 may be disposed between the aseptic filter 139 and the branch point 86 of the sampling channel 64 in the waste liquid channel 138. The waste liquid channel clamp 144 may be configured to open and close the waste liquid channel 138 to switch between allowing the cleaning solution to flow through the waste liquid channel 138 and interrupting the flow of the cleaning solution.

The pressure sensor 146 may be disposed between the branch point 131 and the aseptic filter 136 (upstream of the aseptic filter 136) in the sample introduction channel 130 and may be configured to detect the internal pressure of the sample introduction channel 130 at this position. The detection result detected by the pressure sensor 146 may be wirelessly transmitted to the controller 68. In order to enhance the pressure detection accuracy of the pressure sensor 146, the place where the pressure sensor 146 is to be disposed in the sample introduction channel 130 may have an appropriate shape (e.g., cylindrical shape, disk shape, or the like) having a larger diameter than other portions.

The bubble sensor 148 may be disposed between the connection point 134 and the pressure sensor 146 (upstream of the aseptic filter 136) in the sample introduction channel 130 and may be configured to detect bubbles in the sample introduction channel 130. The detection result detected by the bubble sensor 148 may be wirelessly transmitted to the controller 68. The bubble sensor 148 may be provided upstream of the pressure sensor 146 (on the branch point 131 side).

The controller 68 (control unit) may include a computer that includes one or more processors (not illustrated), a memory, an input/output interface, and/or an electronic circuit. The controller 68 may be configured to control the entire sampling device 60 when the processor executes the program stored in the memory. In at least one example embodiment, the controller 68 may be configured to be able to communicate information with the control circuit 32 of the culturing device 11 and to perform ganged control of the culturing device 11 and the sampling device 60. The controller 68 may be a control device integrated with the control circuit 32 of the culturing device 11.

An example sampling method performed, for example, using the sampling device 60, is described below in reference to FIG. 4. The sampling method may include, for example, a preparation step, a priming step, a sampling step, a cleaning step, and/or a calibration step, which may be sequentially performed.

In the preparation step (step S1), the user of the cell culturing system 10 may set (attaches) the sampling kit 62 to the main mechanism 90 to form the main unit 96 as illustrated in FIG. 3. The user may also set the first detection unit 76 exposed from the housing 91 in the first measuring instrument 110 to construct the first sensor unit 111 and the second detection unit 80 which is similarly exposed in the second measuring instrument 120 to construct the second sensor unit 121. The first sensor unit 111 and the second sensor unit 121 may be suspended from the stand 98.

The user may also set the sample introduction channel 130 in the introduction mechanism 140 to form the introduction unit 141. Thereafter, the user may connect the sampling-device-side connector 132 of the sample introduction channel 130 exposed from the introduction unit 141 to the culturing-device-side connector 56 and may connect the plug of the sample introduction channel 130 to the connection part 84.

Figure 4:
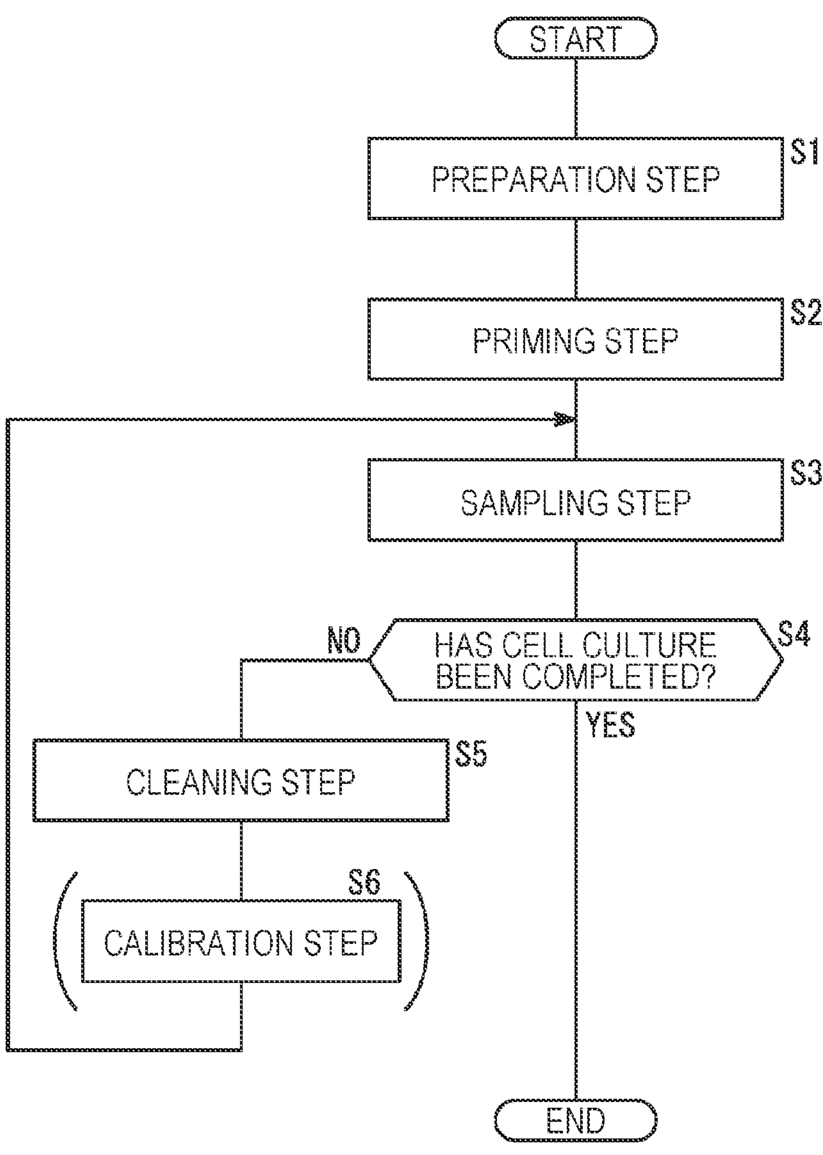
FIG. 4 is a flowchart illustrating a sampling method performed, for example, by the sampling device as illustrated in FIG. 1 in accordance with at least one example embodiment of the present disclosure.
Figure 5:
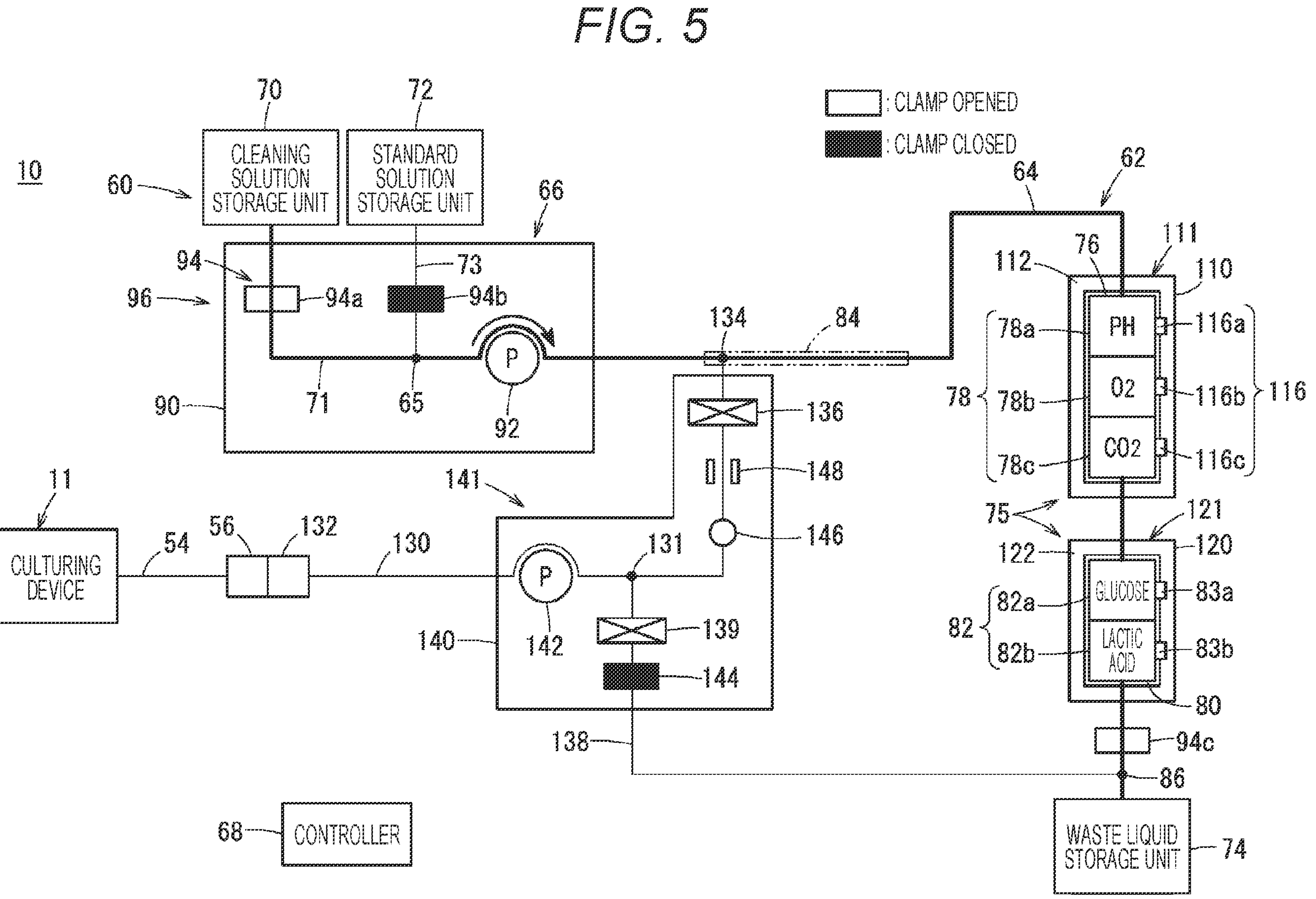
FIG. 5 is a schematic further illustrating operations in the priming step and the cleaning step as illustrated in FIG. 4 in accordance with at least one example embodiment of the present disclosure.

In the priming step (step S2 in FIG. 4), the controller 68 may be configured to cause the cleaning solution clamp 94*a* to open and also the waste liquid clamp 94*c* to open, and may be configured to cause the standard solution clamp 94*b* to close and also the waste liquid channel clamp 144 to close, as illustrated in FIG. 5. With this state, the controller 68 may be configured to rotate the main-mechanism-side pump 92 such that a negative pressure is applied to the cleaning solution branch path 71 so that the cleaning solution is supplied from the cleaning solution storage unit 70. The cleaning solution having passed through the cleaning solution branch path 71 and the branch point 65 may pass through the main-mechanism-side pump 92 in the sampling channel 64 and may sequentially flow through the connection part 84, the first detection unit 76, and/or the second detection unit 80 and may be discharged to the waste liquid storage unit 74. The priming step may also include stopping the rotation of the introduction pump 142 by which the inflow of the cleaning solution into the sample introduction channel 130 can be avoided.

Figure 7:
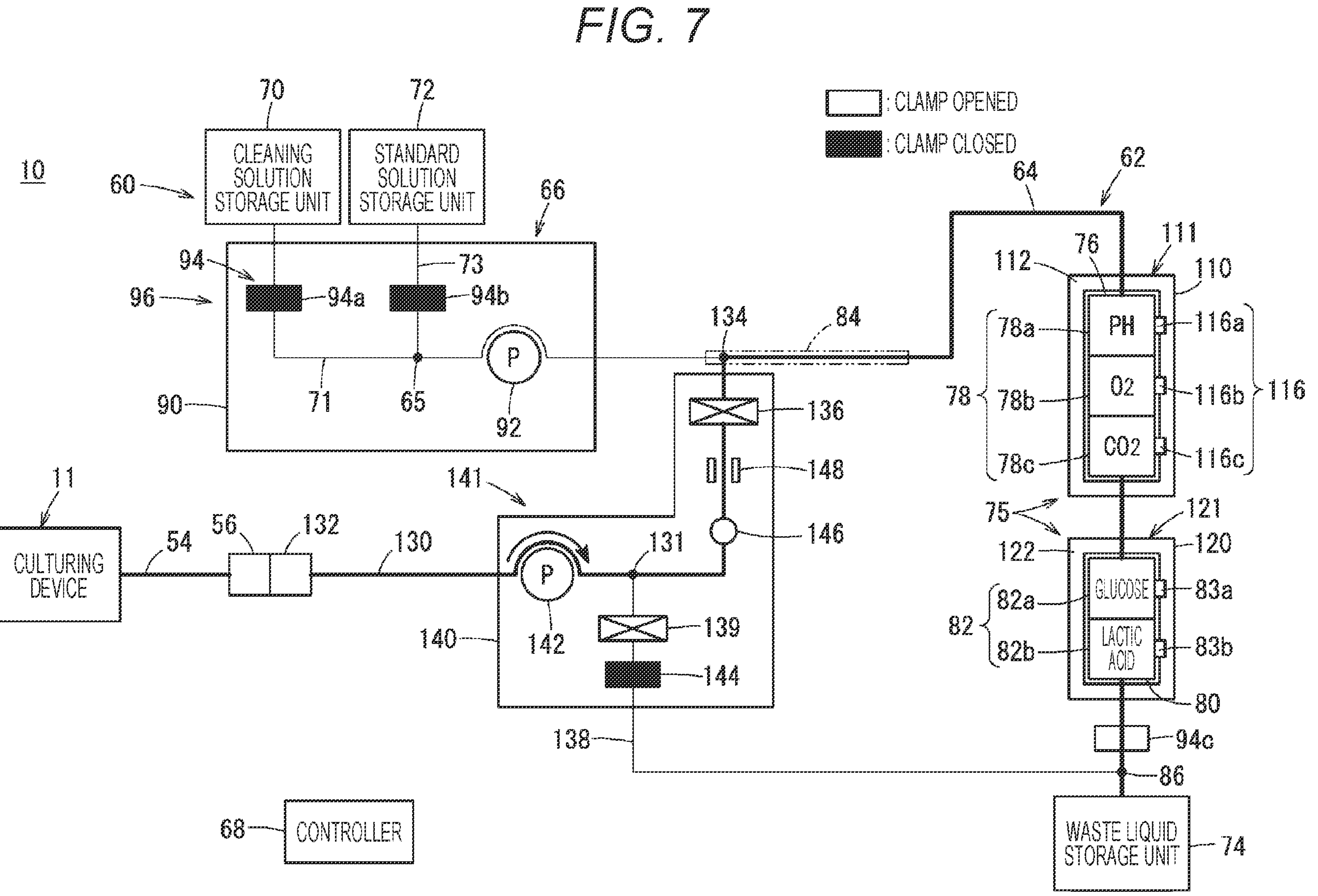
FIG. 7 is a schematic illustrating operations in the main step as illustrated in FIG. 6 in accordance with at least one example embodiment of the present disclosure.

In the sampling step (step S3 in FIG. 4), the sampling device 60 may be configured to guide the sample from the culturing device 11 to the sampling channel 64 and to detect components contained in the sample and amount of the components by the detection unit 75. During this process, the controller 68 may first perform a main step (step S3-1), for example, as illustrated in FIG. 6. In the main step, the controller 68 may be configured to cause the cleaning solution clamp 94*a*, the standard solution clamp 94*b*, and the waste liquid channel clamp 144 to close and to cause the waste liquid clamp 94*c* to open, for example, as illustrated in FIG. 7. The controller 68 may also cause introduction pump 142 to rotate while stopping the rotation of the main-mechanism-side pump 92. Thus, a negative pressure may be applied to the sample introduction channel 130 upstream of the introduction pump 142, whereby the sample may be introduced from the culturing device 11.

The sample drawn from the culturing device 11 may pass through the aseptic filter 136 while flowing through the sample introduction channel 130. Aggregates of proteins and the like contained in the sample may be captured by the aseptic filter 136. In order to enhance the effect of rinsing the aggregates on the aseptic filter 136, the controller 68 may be configured to change the rotation speed of the introduction pump 142 during execution of the main step.

In a first stage after the start of the main step, the controller 68 may be configured to cause the introduction pump 142 to rotate at a first rotation speed which is a high speed so as to allow the sample to flow at a first flow rate. In a second stage after the first stage, the controller 68 may be configured to cause the introduction pump 142 to rotate at a second rotation speed that is lower than the first rotation speed so as to allow the sample to flow at a second flow rate lower than the first flow rate.

Figure 8B:
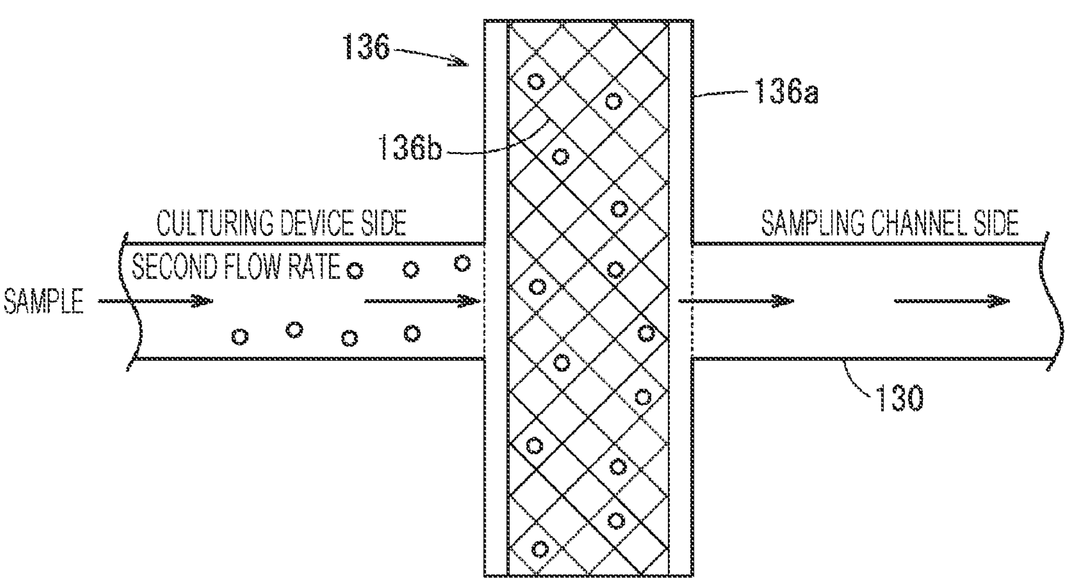
FIG. 8B is a schematic illustrating movement of aggregates with respect to the aseptic filter in a second stage of the main step as illustrated in FIG. 6 in accordance with at least one example embodiment of the present disclosure.

In at least one example embodiment, the first flow rate (first rotation speed) may three times to ten times the second flow rate (second rotation speed). The first flow rate may be in a range of about 20 mL/min to about 60 mL/min. The second flow rate may be in a range of about 1 mL/min to about 10 mL/min. In the first stage, the aggregate on the filter surface on the sampling channel 64 side captured in the previous adhering substance removal step may flow out to the sampling channel 64, for example, as illustrated in FIG. 8A. In the second stage, the sample may be allowed to gently flow and guided to the sampling channel 64, whereby it is possible to reduce excessive capture of the aggregates on the filter surface on the culturing device 11 side, for example, as illustrated in FIG. 8B.

The controller 68 may be configured to set a period for executing the first stage to about several seconds (for example, 1 to 3 seconds) and to set a period for executing the second stage so that a predetermined sample amount can be obtained. By performing the first stage in a short period after the start of the main step, it may be possible to enhance the effect of washing away the aggregates captured on the filter surface on the sampling channel 64 side and to reduce excessive capture of the aggregates on the filter surface on the culturing device 11 side. The controller 68 may be configured to change the flow rate of the sample (the rotation speed of the introduction pump 142) stepwise in three or more stages or may be configured to linearly (linearly) change the flow rate from the first flow rate to the second flow rate.

As illustrated in FIG. 7, the sample in the sample introduction channel 130 passing through the aseptic filter 136 may sequentially flow through the connection part 84 (connection point 134), the first detection unit 76, and/or the second detection unit 80 and may be discharged to the waste liquid storage unit 74. When the sample passes, the plurality of first elements 78 (e.g., pH chip 78*a*, $O_2$ chip 78*b*, and/or $CO_2$ chip 78*c*) of the first detection unit 76 comes into contact with the sample and may be colored according to the pH and/or the contents of $O_2$ and/or $CO_2$. The first measuring instrument 110 may be configured to optically measure each of the first elements 78 and to transmit the detection result to the controller 68. The controller 68 that has received the detection result may be configured to perform appropriate processing to display the measured values (e.g., pH value, $O_2$ concentration, and/or $CO_2$ concentration) on the monitor 100 of the main mechanism 90.

When the sample passes, the plurality of second elements 82 (e.g., glucose chip 82*a* and/or lactic acid chip 82*b*) of the second detection unit 80 may come into contact with the sample, and the second measuring instrument 120 may be configured to detect current values corresponding to the contents of glucose and/or lactic acid. The second measuring instrument 120 may be configured to transmit each detection result to the controller 68. The controller 68 that has received the detection result may be configured to perform appropriate processing to display the measured values (e.g., glucose concentration and/or lactic acid concentration) on the monitor 100.

With renewed reference to FIG. 6, the controller 68 may be configured to determine whether to end the main step during the execution of the main step (step S3-2). For example, the controller 68 may be configured to determine to end the sampling step on the basis of completion of detection of the sample by the detection unit 75 and to display of the detection result or on the basis of execution of the sampling step for a predetermined time.

The controller 68 may be configured to detect the pressure in the sample introduction channel 130 by the pressure sensor 146 and to detect bubbles in the sample introduction channel 130 by the bubble sensor 148 during the execution of the main step (step S3-3). The controller 68 may be configured to determine whether or not the aseptic filter 136 is clogged by the sample flowing through the sample introduction channel 130 on the basis of the detected pressure and/or the detected bubbles (step S3-4). For example, the controller 68 may determine that the aseptic filter 136 is clogged when the pressure detected by the pressure sensor 146 becomes equal to or lower than a predetermined pressure threshold (not illustrated). Alternatively, the controller 68 may determine that the aseptic filter 136 is clogged when the number of bubbles included in the sample is equal to or greater than a prescribed number as a result of detection by the bubble sensor 148 during the sampling step.

Figure 9:
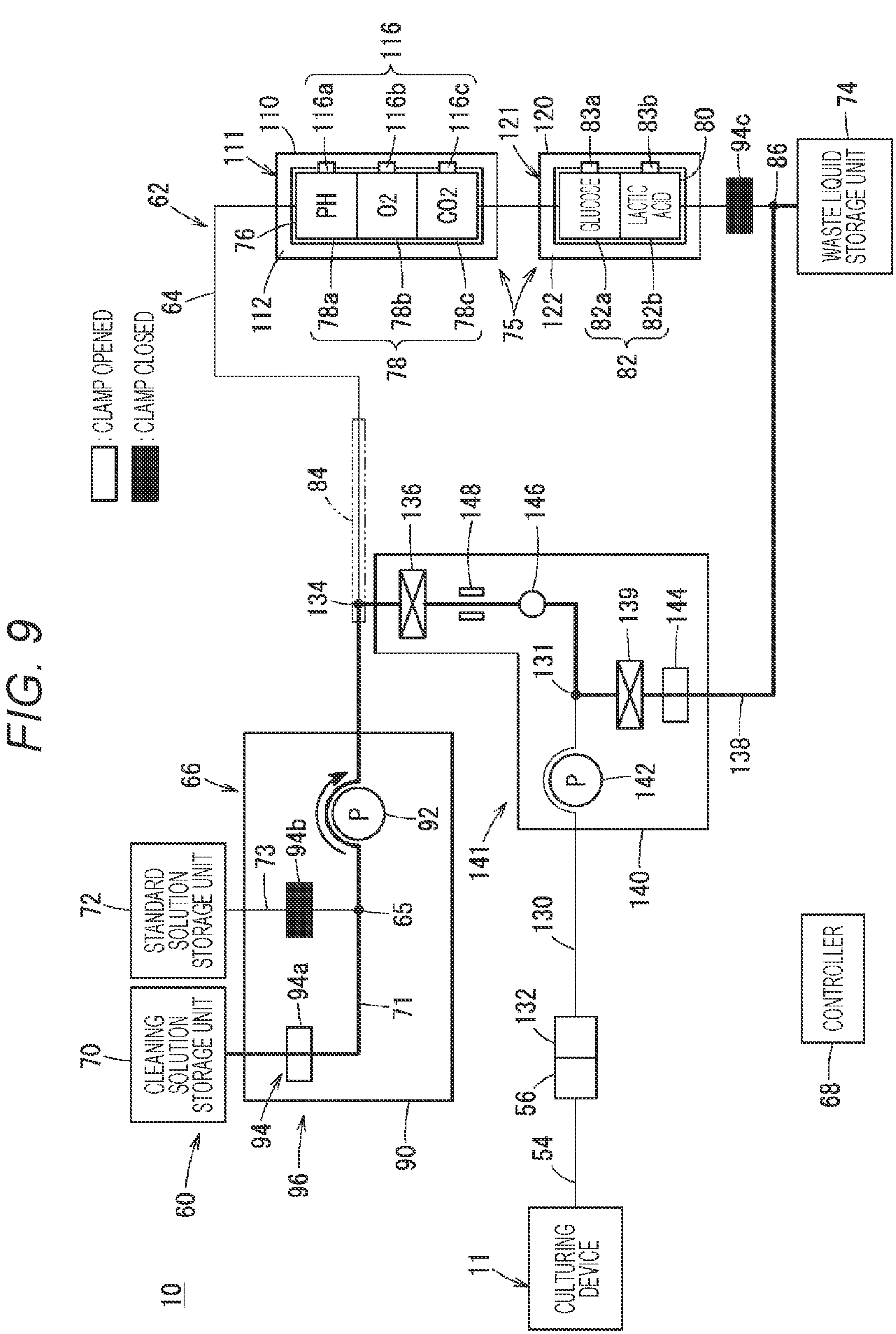
FIG. 9 is a schematic illustrating operations in the adhering substance removal step as illustrated in FIG. 6 in accordance with at least one example embodiment of the present disclosure.

When the aseptic filter 136 is not clogged (step S3-4: NO), the processing may return to step S3-1 and the same processing flow may be repeated. When it is determined that the aseptic filter 136 is clogged (step S3-4: YES), the controller 68 may stop the main step and may perform the adhering substance removal step (step S3-5) for removing aggregates of the aseptic filter 136. In the adhering substance removal step, the controller 68 may be configured to cause the standard solution clamp 94*b* and the waste liquid clamp 94*c* to close and to cause the cleaning solution clamp 94*a* and the waste liquid channel clamp 144 to open, for example, as illustrated in FIG. 9. The controller 68 may also cause main-mechanism-side pump 92 to rotate while stopping the rotation of the introduction pump 142.

During the adhering substance removal step, the controller 68 may be configured to maintain the rotation speed of the main-mechanism-side pump 92 constant and to introduce the cleaning solution into the sample introduction channel 130 at a constant flow rate. As a result, the cleaning solution in the cleaning solution storage unit 70 may be introduced into the sampling channel 64 through the cleaning solution branch path 71. Since the waste liquid clamp 94*c* is closed, the cleaning solution may flow into the sample introduction channel 130 from the connection point 134 without flowing toward the detection unit 75. The cleaning solution flowing into the sample introduction channel 130 may pass through the aseptic filter 136 from the sampling channel 64 side to the culturing device 11 side, so that the aggregates adhering to the aseptic filter 136 can be removed.

The cleaning solution containing the aggregates may flow from the branch point 131 to the waste liquid channel 138 as a result of the waste liquid channel clamp 144 being opened and the introduction pump 142 being stopped. In the waste liquid channel 138, aggregates may be removed from the cleaning solution as the cleaning solution passes through the aseptic filter 139. Then, the cleaning solution may return from the waste liquid channel 138 to the sampling channel 64 through the branch point 86, may flow through the sampling channel 64, and may be discharged to the waste liquid storage unit 74.

The sampling device 60 may be satisfactorily eliminate clogging of the aseptic filter 136 by performing the adhering substance removal step according to the state of the sample during the sampling step. After performing the adhering substance removal step for a predetermined period, the controller 68 may return to the main step (step S3-1) as illustrated in FIG. 6 and may perform the main step from the beginning. As a result, the sampling device 60 can introduce a specified amount of samples that can be satisfactorily detected by the detection unit 75 into the sampling channel 64.

It should be appreciated that the adhering substance removal step is not limited to be performed according to the state of the sample during the sampling step and may be periodically performed, for example, after the sampling step and/or after a cleaning step. In addition, the controller 68 may also be configured to change the rotation speed of the main-mechanism-side pump 92 during the execution of the adhering substance removal step as in the main step.

In the first stage after the start of the adhering substance removal step, the controller 68 may be configured to cause the main-mechanism-side pump 92 to rotate at the first rotation speed, which may be a high speed, to allow the cleaning solution to flow at the first flow rate. In the second stage after the first stage, the controller 68 may be configured to cause the main-mechanism-side pump 92 to rotate at the second rotation speed that is lower than the first rotation speed so as to allow the cleaning solution to flow at the second flow rate lower than the first flow rate. The period for executing the first stage may be shorter than the period for executing the second stage. As a result, in the first stage, the aggregates adhering to the aseptic filter 136 may be more easily removed and the aggregates captured in the previous adhering substance removal step may easily pass through the aseptic filter 139.

With renewed reference to FIG. 4, after the sampling step, the controller 68 may be configured to determine whether or not the cell culture of the culturing device 11 is completed (step S4). When the cell culture is not completed (step S4: NO), the cleaning step (step S5) may be performed. In the cleaning step, the controller 68 may be configured to supply the cleaning solution from the cleaning solution storage unit 70 to the sampling channel 64, for example, as in the priming step as illustrated in FIG. 5. As a result, the sample attached to the plurality of first elements 78 (e.g., pH chip $78_a$, $O_2$ chip 78*b*, and/or $CO_2$ chip 78*c*) and the plurality of second elements 82 (e.g., glucose chip 82*a* and/r lactic acid chip 82*b*) may be removed by the cleaning solution.

The sampling device 60 may be configured to perform a calibration step (step S6) as necessary. In the calibration step, the controller 68 may be configured to cause the main-mechanism-side pump 92 to rotate where the standard solution clamp 94*b* and the waste liquid clamp 94*c* are opened and the cleaning solution clamp 94*a* and the waste liquid channel clamp 144 are closed. As a result, the standard solution in the standard solution storage unit 72 may be guided to the sampling channel 64 from the standard solution branch path 73, sequentially flows through the connection part 84, the first detection unit 76, and/or the second detection unit 80 and may be discharged to the waste liquid storage unit 74.

The second sensor unit 121 may be configured to measure the glucose concentration and/or the lactic acid concentration in the standard solution and to transmit the measurement results to the controller 68 or the second measuring instrument 120. The controller 68 or the second measuring instrument 120 may calibrate the second measuring instrument 120 on the basis of the measurement result of the second sensor unit 121. The first sensor unit 111 (first measuring instrument 110) may be set in the calibration device 118 by the user. The first measuring instrument 110 may be configured to measure the pH, the 02 concentration, and/or the $CO_2$ concentration of the standard solution in the calibration device 118 and to transmit the measurement results to the controller 68 or the first measuring instrument 110. The controller 68 and/or the first measuring instrument 110 may perform calibration of each of the pH detector 116*a*, the 02 detector 116*b*, and/or the $CO_2$ detector 116*c* on the basis of the measurement results.

When the cleaning step (or the calibration step) is completed, the controller 68 may return to step S3 and may sequentially perform the subsequent steps. On the other hand, when determining in step S4 that the cell culture is completed (step S4: YES), the controller 68 may end the operation flow of the sampling device 60.

It should be appreciated that the sampling device 60 and the sampling method are not limited to the above, and various methods can be adopted. For example, the waste liquid channel 138 of the sampling device 60 may not be connected to the sampling channel 64 but may be connected to a waste liquid collection unit (not illustrated) different from the waste liquid storage unit 74. The waste liquid channel 138 may not include the aseptic filter 139.

Figure 10:
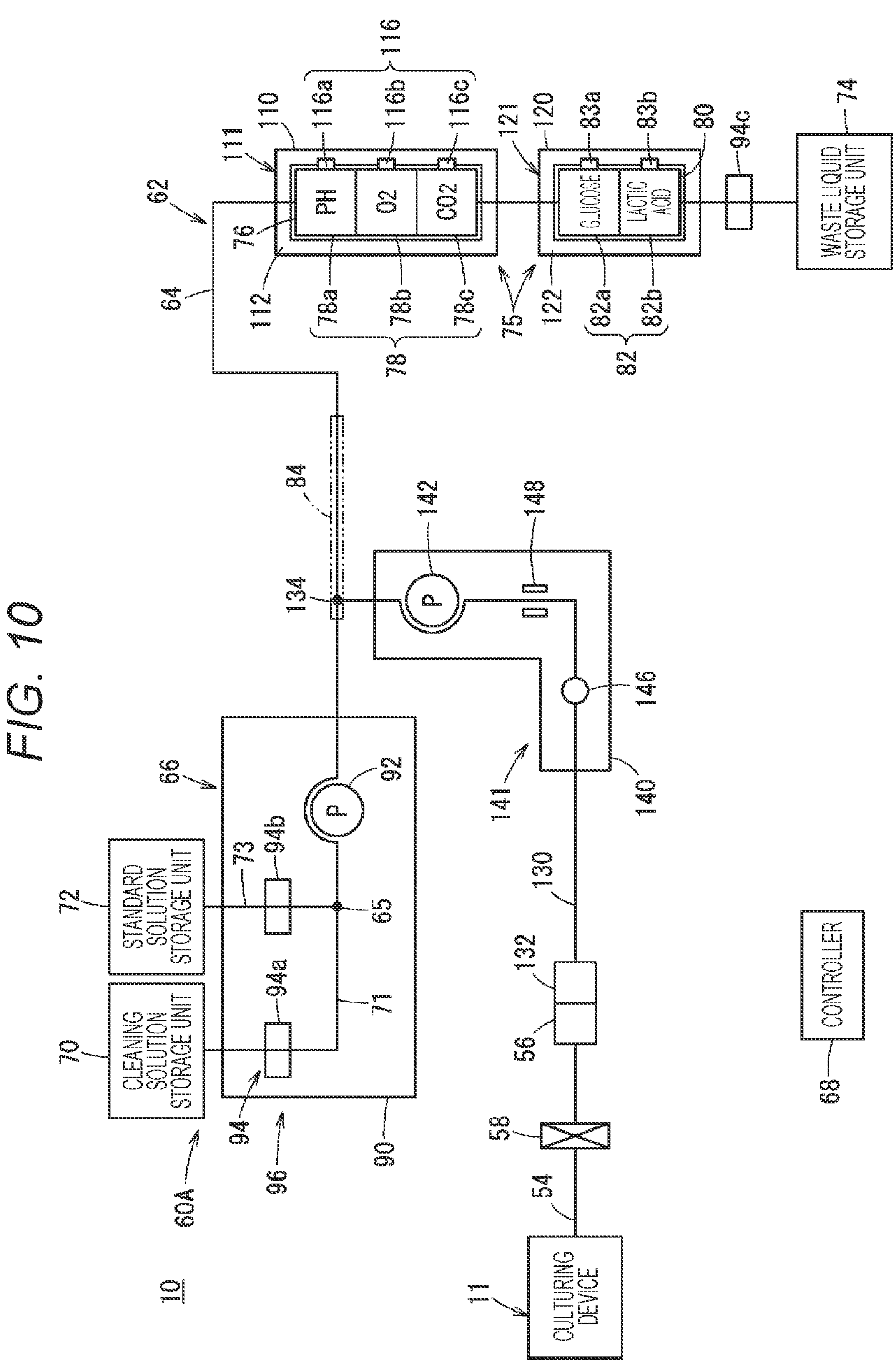
FIG. 10 is a schematic illustrating another example channel of the sampling device as illustrated in FIG. 1 in accordance with at least one example embodiment of the present disclosure.

A sampling device 60A according to another example embodiment of the present disclosure may differ from the sampling device 60 in that a cleaning solution may be guided to the culturing device 11 without providing the waste liquid channel 138 in the sample introduction channel 130, for example, as illustrated in FIG. 10. In the following description, components or steps that are the same and/or having the same functionality as those in the instance of sampling device 60 are given the same reference numerals.

An introduction unit 141 of the sampling device 60A may include an introduction pump 142 near a connection point 134 of the sample introduction channel 130. The introduction pump 142 may be rotatable in a first direction in which the sample is guided to the sampling channel 64 and in a second direction in which the cleaning solution is drawn into the sample introduction channel 130.

In at least one example embodiment, the introduction unit 141 may also include a pressure sensor 146 and/or a bubble sensor 148 in the sample introduction channel 130 upstream of the introduction pump 142. The culturing device 11 may be provided with an aseptic filter 58 that helps to bring the culturing device 11 side into an aseptic state. The aseptic filter 58 may be provided between the EC circulation circuit 44*a* and the culturing-device-side connector 56 (see also FIG. 2).

In at least one example embodiment, an example sampling method performed, for example, by the sampling device 60A, may be the same as the example sampling method performed by the sampling device 60 as illustrated in FIG. 4 except that in the cleaning step opening and closing of the waste liquid channel clamp 144 are not performed, since this clamp is not provided.

For example, in the sampling step (main step), the controller 68 of the sampling device 60A may be configured to cause the cleaning solution clamp 94*a* and the standard solution clamp 94*b* to close and to cause the waste liquid clamp 94*c* to open. The controller 68 may also cause the introduction pump 142 to rotate in the first direction while stopping the rotation of the main-mechanism-side pump 92. As a result, the sample introduced from the culturing device 11 and into the sample introduction channel 130 may flow into the sampling channel 64 from the connection point 134, may sequentially flow through the first detection unit 76 and/or the second detection unit 80, and may be discharged to the waste liquid storage unit 74.

In the main step, the controller 68 may be configured to cause the rotation speed of the introduction pump 142 to change, as discussed above. For example, in a first stage after the start of the main step, the controller 68 may be configured to cause the introduction pump 142 to rotate at a first rotation speed, which may be a high speed, so to allow the sample to flow at a first flow rate. In a second stage, for example, after the first stage, the controller 68 may be configured to cause the introduction pump 142 to rotate at a second rotation speed, which may be lower than the first rotation speed, to allow the sample to flow at a second flow rate that may be lower than the first flow rate. Thus, it may be possible to enhance the effect of washing away the aggregates captured on the filter surface on the sampling channel 64 side and to also reduce excessive capture of the aggregates on the filter surface on the culturing device 11 side (see also FIGS. 8A and 8B).

Figure 11:
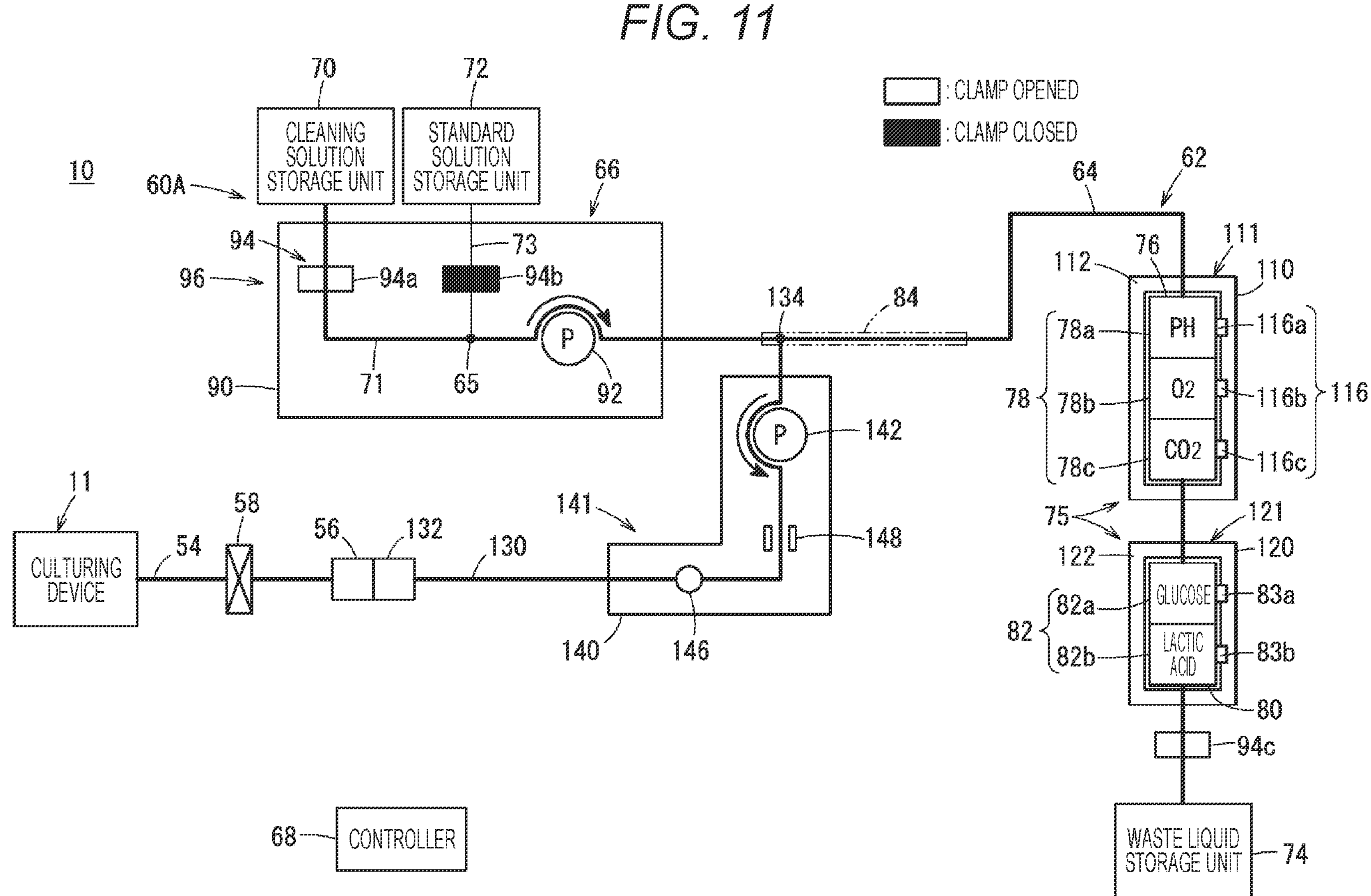
FIG. 11 is a schematic illustrating a cleaning step and an adhering substance removal step performed, for example, by the sampling device as illustrated in FIG. 10 in accordance with at least one example embodiment of the present disclosure.

In the cleaning step, the controller 68 may be configured to cause the cleaning solution clamp 94*a* and the waste liquid clamp 94*c* to open and to cause the standard solution clamp 94*b* to close, for example, as illustrated in FIG. 11. The controller 68 may also be configured to cause the introduction pump 142 to rotate in the second direction while causing the main-mechanism-side pump 92 to rotate. As a result, the cleaning solution in the cleaning solution storage unit 70 may flow out from the cleaning solution branch path 71 to the sampling channel 64 and may be divided into a first cleaning solution directly flowing through the sampling channel 64 from the connection point 134 and a second cleaning solution flowing into the sample introduction channel 130 from the connection point 134.

The first cleaning solution may flow through the detection unit 75 (e.g., first detection unit 76 and/or second detection unit 80) to clean the plurality of first elements 78 and/or the plurality of second elements 82. When flowing through the sample introduction channel 130 into the sample outflow channel 54, the second cleaning solution may pass through the aseptic filter 58. The second cleaning solution may remove aggregates adhering to the aseptic filter 58 when passing through the aseptic filter 58. The second cleaning solution that passes through the aseptic filter 58 may flow through the EC circulation circuit 44*a* of the culturing device 11, however, the amount thereof may be small and discharged to the waste liquid unit 20 via the EC waste liquid circuit 48.

In the cleaning step, the controller 68 may be configured to set the rotation speed of the introduction pump 142 in the second direction to be lower than the rotation speed of the main-mechanism-side pump 92. As a result, an amount of the second cleaning solution that flows through the sample introduction channel 130 may be smaller than an amount of the first cleaning solution that flows through the sampling channel 64. Therefore, the second cleaning solution that flows into the culturing device 11 can be sufficiently reduced. In at least one example embodiment, the controller 68 may be configured to cause the rotation speed of the introduction pump 142 to change during the cleaning step, as described above.

The sampling device 60A may be configured to simultaneously perform the cleaning step and the adhering substance removal step by reversing the rotation direction of the introduction pump 142. Thus, the sampling device 60A (sampling kit 62) may have a simpler configuration and the workability and handleability for the user can be improved.

Figure 12:
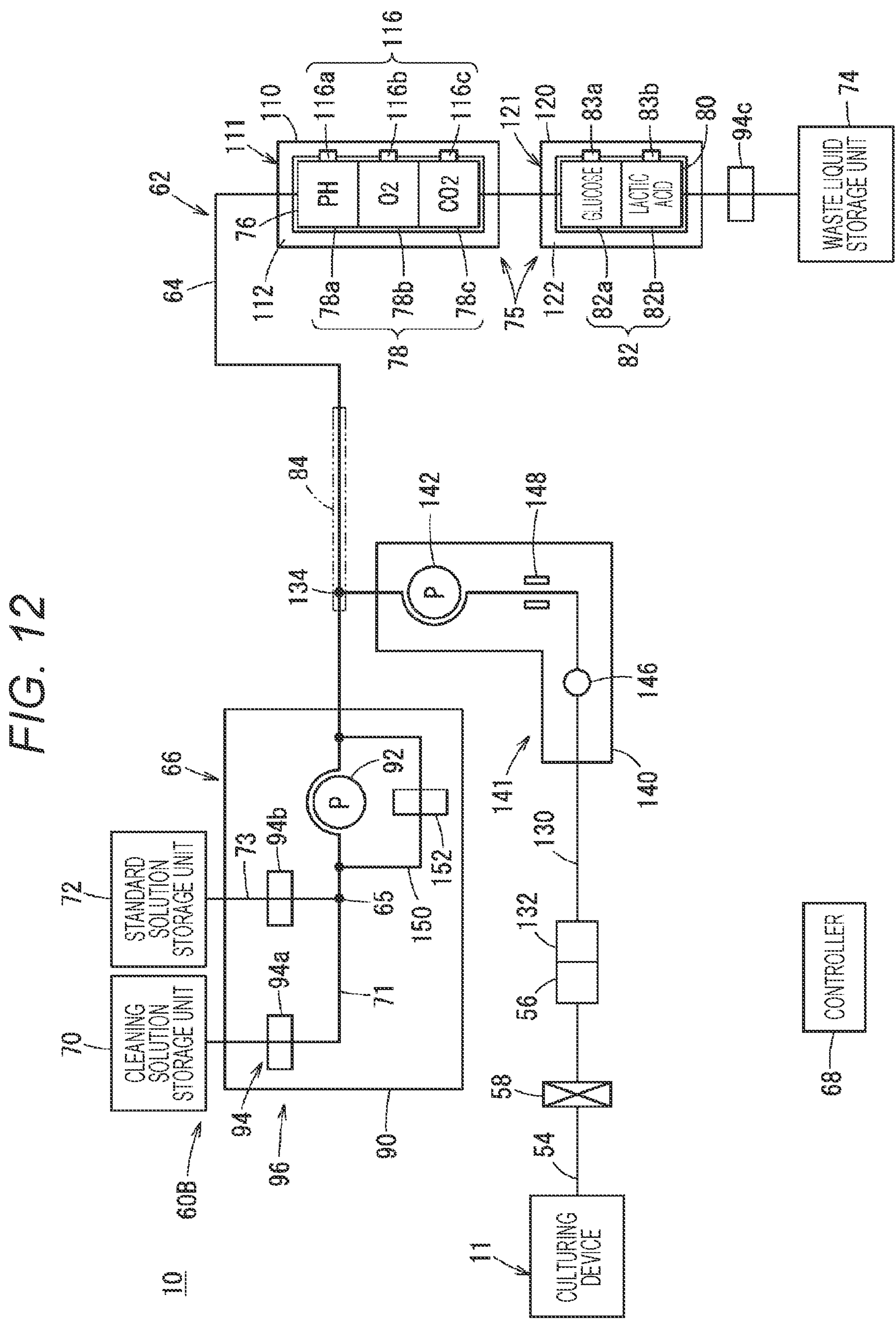
FIG. 12 is a schematic illustrating another example channel of the sampling device as illustrated in FIG. 1 in accordance with at least one example embodiment of the present disclosure.

A sampling device 60B according to another example embodiment of the present disclosure may differ from the sampling device 60A in that a bypass channel 150 configured to bypass the main-mechanism-side pump 92 may be connected to the sampling channel 64, for example, as illustrated in FIG. 12. The bypass channel 150 may be provided with a bypass channel clamp 152 that is configured to open and close the bypass channel 150. The bypass channel clamp 152 may be provided in the main mechanism 90 and may be configured to open and close the flow path of the bypass channel 150 under the direction of the controller 68.

The sampling device 60B may be configured to perform the adhering substance removal step at a timing different from the timing at which the cleaning step is performed. For example, the controller 68 of the sampling device 60B may be configured to shift to the adhering substance removal step on the basis of the pressure detected by the pressure sensor 146 and/or bubbles detected by the bubble sensor 148 during the execution of the sampling step.

Figure 13:
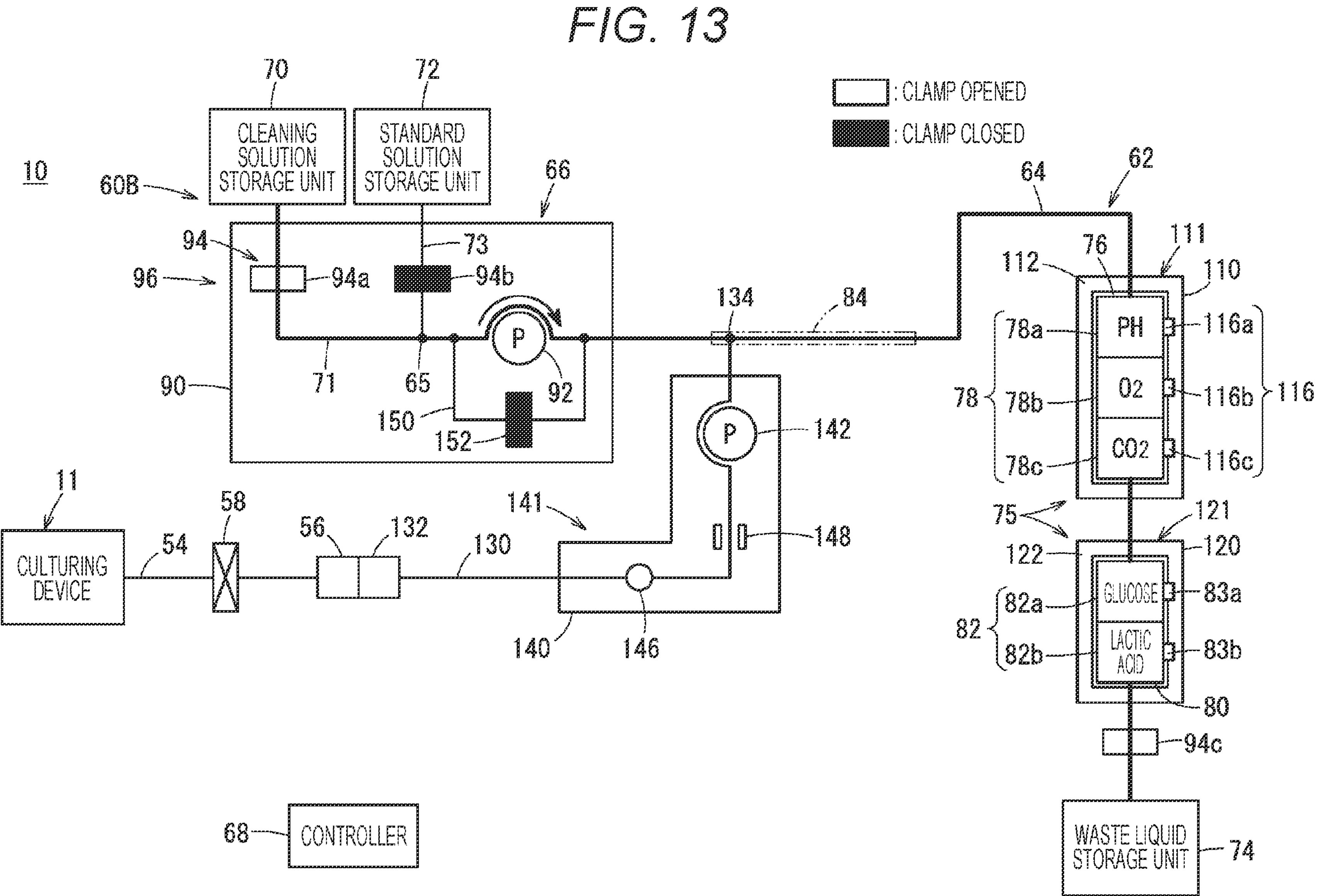
FIG. 13 is a schematic illustrating a cleaning step performed by the sampling device as illustrated in FIG. 12 in accordance with at least one example embodiment of the present disclosure.

In the cleaning step, the controller 68 may be configured to cause the cleaning solution clamp 94*a* and the waste liquid clamp 94*c* to open and to cause the standard solution clamp 94*b* and the bypass channel clamp 152 to close, for example, as illustrated in FIG. 13. The controller 68 may be configured to cause the rotation of the introduction pump 142 to stop while rotating the main-mechanism-side pump 92. Thus, the cleaning solution in the cleaning solution storage unit 70 may flow to the first detection unit 76 and/or the second detection unit 80 through the sampling channel 64 in which the main-mechanism-side pump 92 is disposed.

Figure 14:
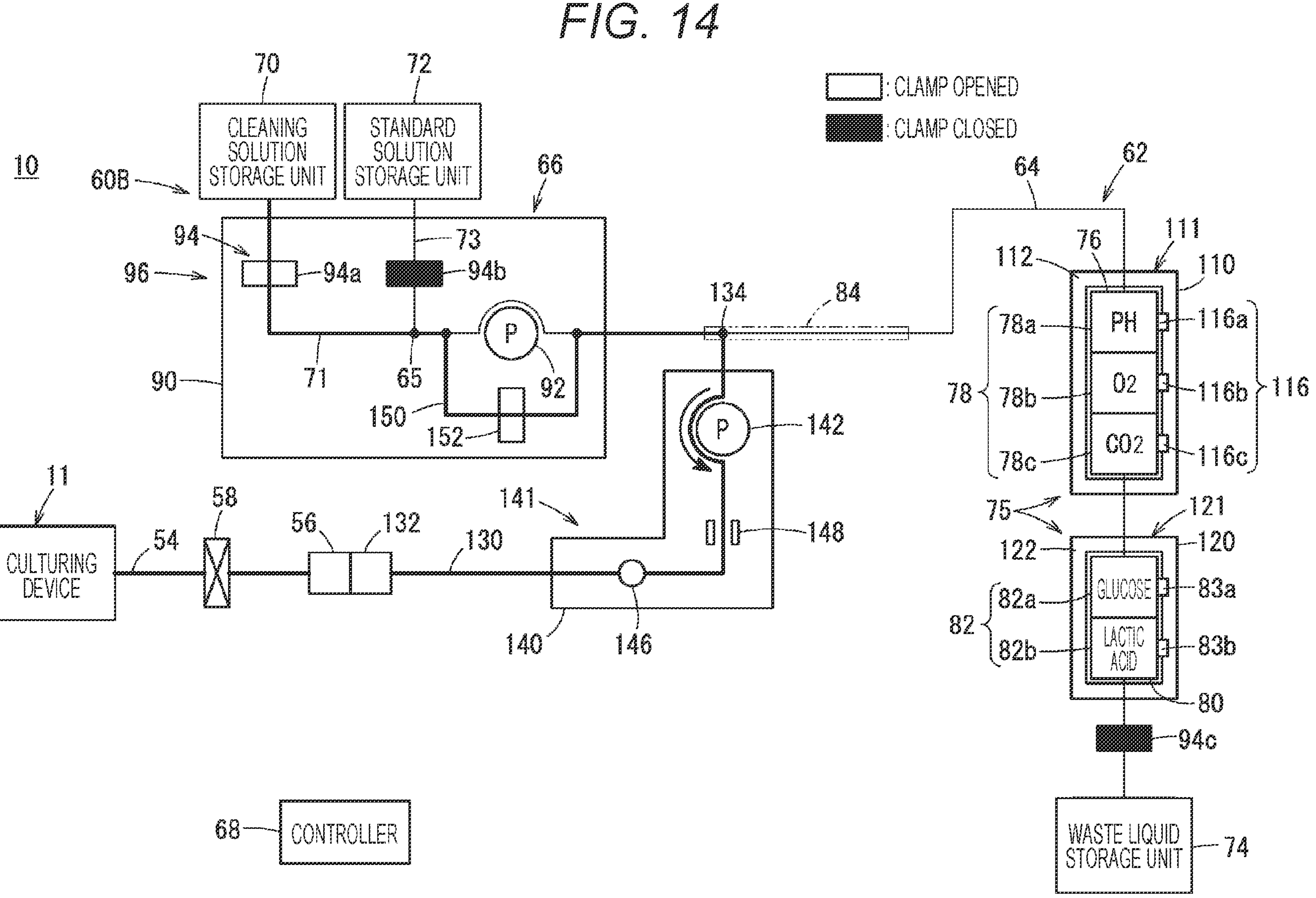
FIG. 14 is a schematic illustrating an adhering substance removal step performed, for example, by the sampling device as illustrated in FIG. 12 in accordance with at least one example embodiment of the present disclosure.

In the adhering substance removal step, the controller 68 may be configured to cause the cleaning solution clamp 94*a* and the bypass channel clamp 152 to open and to cause the standard solution clamp 94*b* and the waste liquid clamp 94*c* to close, for example, as illustrated in FIG. 14. The controller 68 may also be configured to cause the introduction pump 142 to rotate in the second direction while causing the rotation of the main-mechanism-side pump 92 to stop. Thus, the cleaning solution from the cleaning solution storage unit 70 may flow through the sampling channel 64 while passing through the bypass channel 150 and may flow into the sample introduction channel 130. Therefore, aggregates on the aseptic filter 58 in the culturing device 11 may be removed as the liquid moves from the sample introduction channel 130 side to the EC circulation circuit 44*a* side.

The sampling device 60B, including the bypass channel 150 and the bypass channel clamp 152, may guide the cleaning solution to the aseptic filter 58 only by the rotation of the introduction pump 142 to remove aggregates. The sampling device 60B may also be configured to change the rotation speed of the introduction pump 142 in the adhering substance removal step.

Figure 15:
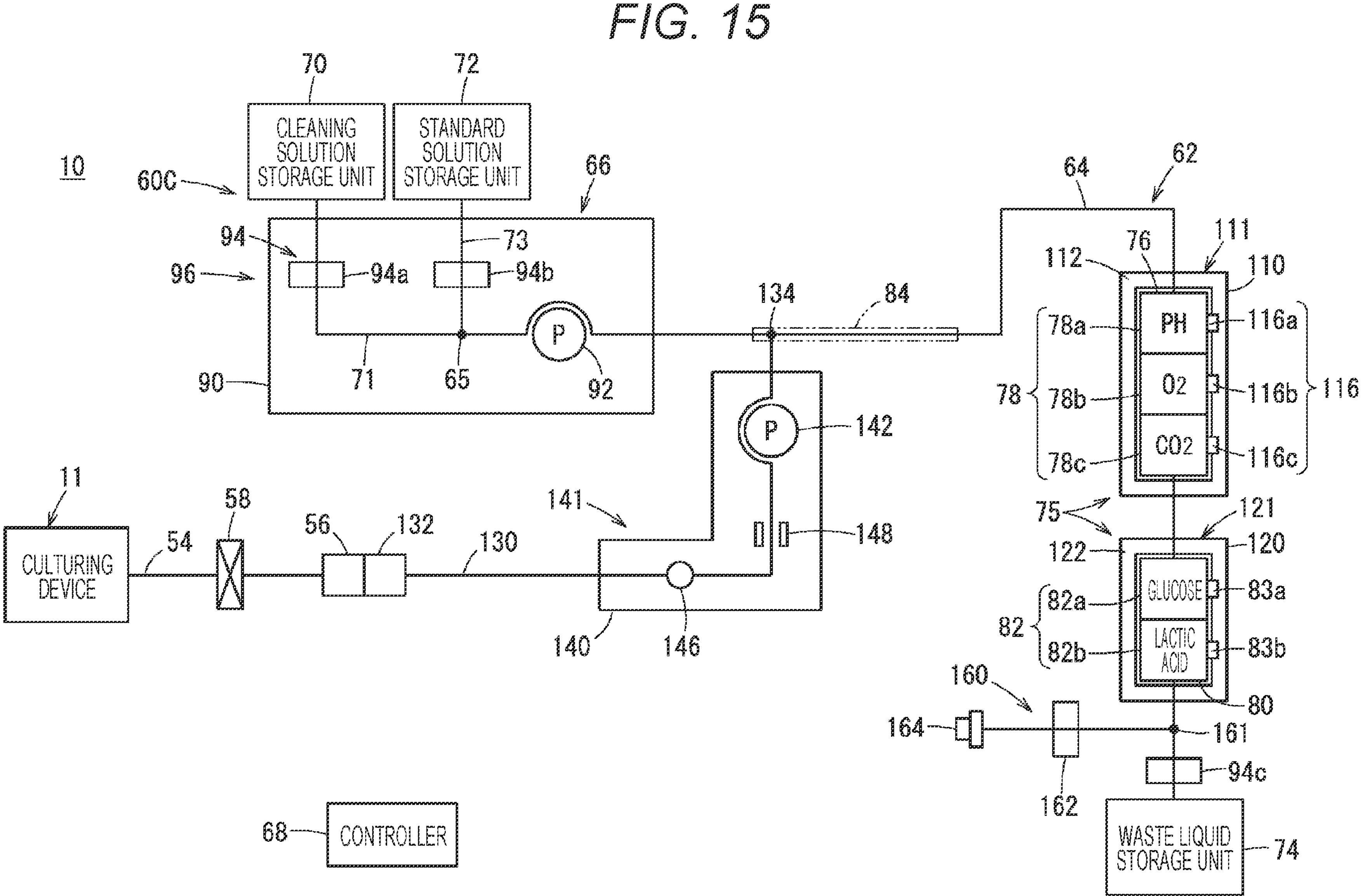
FIG. 15 is a schematic schematically illustrating another example channel of the sampling device as illustrated in FIG. 1 in accordance with at least one example embodiment of the present disclosure.

A sampling device 60C according to another example embodiment of the present disclosure may differ from the sampling device 60A in that the sampling device 60A includes an air port 160 through which air can be taken into a sampling channel 64 and also an air port clamp 162 that is configured to open and close the air port 160, for example, as illustrated in FIG. 15. That is, the sampling device 60C may be configured to remove aggregates of the aseptic filter 58 of the culturing device 11 by allowing air to flow in through the air port 160 to push back the culture medium in the sampling channel 64 and the sample introduction channel 130.

The air port 160 may be connected to a branch point 161 provided in the sampling channel 64 downstream of the detection unit 75 (e.g., between the second detection unit 80 and the waste liquid storage unit 74). The air port 160 may include an air filter 164 at an end extending from the sampling channel 64. The air filter 164 may be configured to interrupt outflow of liquid from the sampling channel 64 and to allow air to flow into the sampling channel 64.

The air port clamp 162 may be provided in the main mechanism 90 and may be configured to open and close the flow path of the air port 160 under the direction of the controller 68. In the sample introduction channel 130, the pressure sensor 146 and/or the bubble sensor 148 may be disposed on the upstream side of the introduction pump 142, as in the instance of sampling device 60A.

Providing the air filter 164 at the branch point 161 can help to ensure that a great amount of liquid is available for cleaning the filter.

In at least one example embodiment, an example sampling method performed, for example, by the sampling device 60C, may be the same as the example sampling method performed by the sampling device 60, sampling device 60A, and/or sampling device 60C, as illustrated above, except that the adhering substance removal step may differ. In the example sampling method performed, for example, by the sampling device 60C, the adhering substance removal step may be performed at a timing different from that of the cleaning step.

Figure 16:
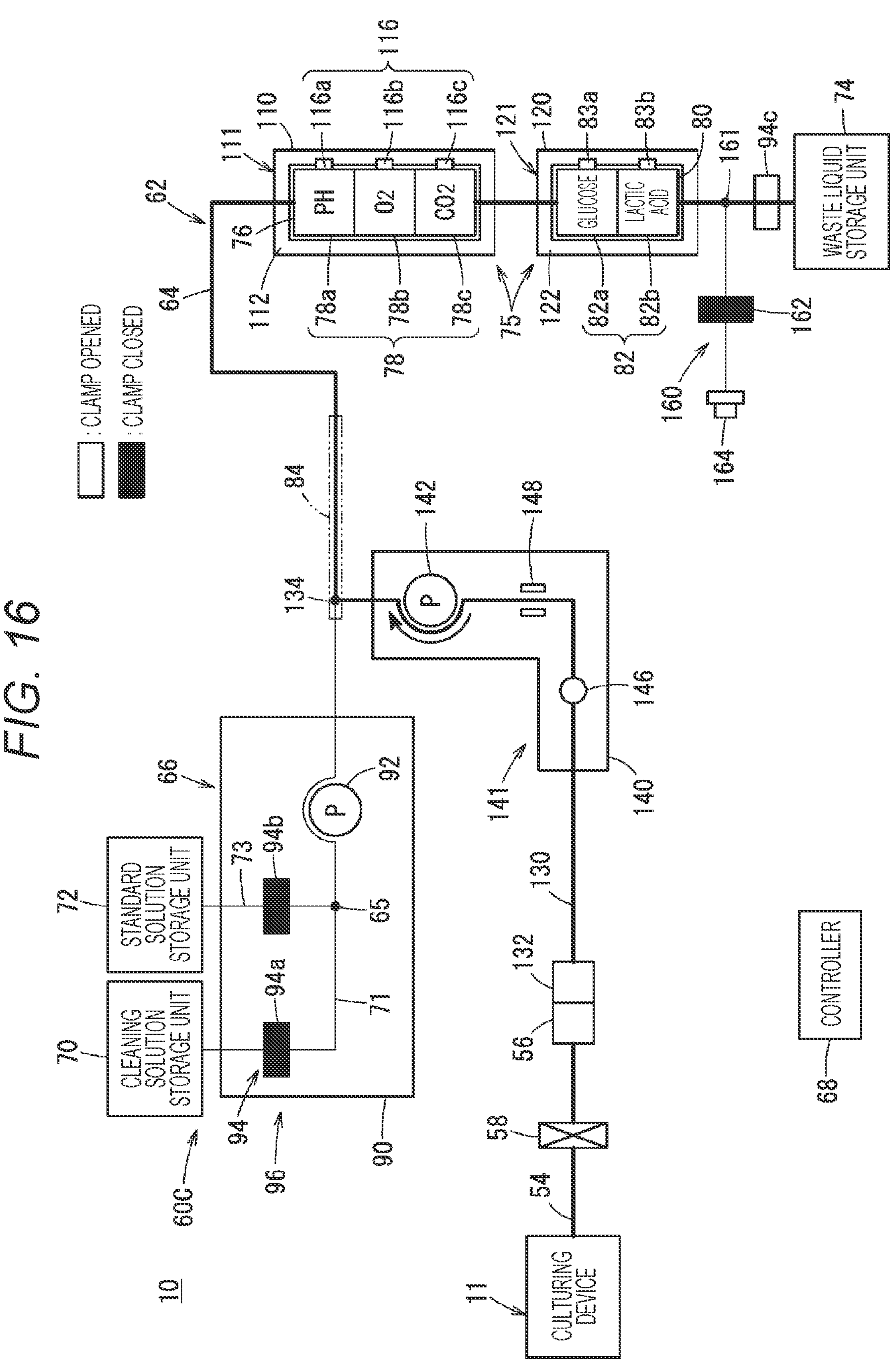
FIG. 16 is a schematic illustrating a main step performed, for example, by the sampling device as illustrated in FIG. 15 in accordance with at least one example embodiment of the present disclosure.

In the sampling step (main step), the controller 68 of the sampling device 60C may be configured to cause the cleaning solution clamp 94*a*, the standard solution clamp 94*b*, and the air port clamp 162 to close and to cause the waste liquid clamp 94*c* to open, for example, as illustrated in FIG. 16. The controller 68 may also be configured to cause the introduction pump 142 to rotate in the first direction while stopping the rotation of the main-mechanism-side pump 92. The controller 68 may be configured to cause the rotation speed of the introduction pump 142 to change, as described above. As a result, the sample introduced from the culturing device 11 and into the sample introduction channel 130 may flow into the sampling channel 64 from the connection point 134, may sequentially flow through the first detection unit 76 and/or the second detection unit 80, and may be discharged to the waste liquid storage unit 74.

Figure 17:
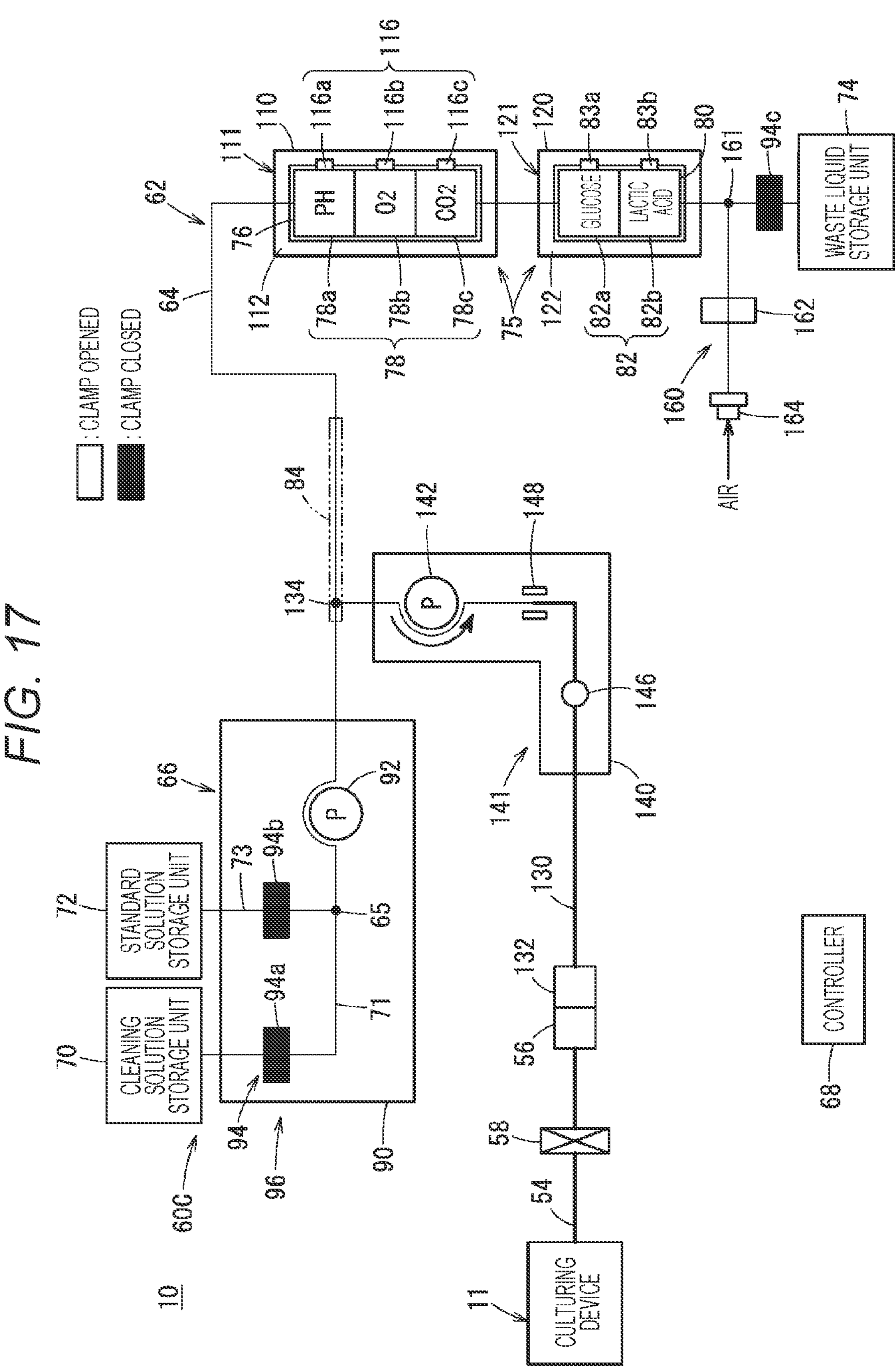
FIG. 17 is a schematic illustrating an adhering substance removal step performed, for example, by the sampling device as illustrated in FIG. 15 in accordance with at least one example embodiment of the present disclosure.

In the adhering substance removal step, the controller 68 may be configured to cause the air port clamp 162 to open and to cause the cleaning solution clamp 94*a*, the standard solution clamp 94*b*, and the waste liquid clamp 94*c* to close, for example, as illustrated in FIG. 17. Then, the controller 68 may be configured to cause the rotation of the main-mechanism-side pump 92 to stop and to cause the introduction pump 142 to rotate in the second direction. Due to the rotation of the introduction pump 142, a negative pressure may be applied to the sample introduction channel 130 and the sampling channel 64 downstream of the introduction pump 142. As a result, air may flow into the sampling channel 64 through the air port 160 (air filter 164).

The sample (culture medium) remaining in the sampling channel 64 and the sample introduction channel 130 may flow toward the culturing device 11 under the rotation of the introduction pump 142 in the second direction. This culture medium may pass through the aseptic filter 58 in the sample outflow channel 54 of the culturing device 11 (see also FIG. 2) thereby removing aggregates adhering to the aseptic filter 58.

During the adhering substance removal step, the controller 68 may be configured to monitor whether or not the air flowing into the sampling channel 64 through the air port 160 reaches the bubble sensor 148 on the basis of the detection signal of the bubble sensor 148. When detecting air by the bubble sensor 148, the controller 68 may be configured to cause the rotation of the introduction pump 142 to stop and the adhering substance removal step to end. As a result, the sampling device 60C may avoid air from reaching the aseptic filter 58 while removing the aggregates on the aseptic filter 58 of the culturing device 11 by the culture medium. The sampling device 60C may reliably prevent the inflow of the cleaning solution into the culturing device 11 by not using the cleaning solution in the adhering substance removal step.

It should be appreciated that the features discussed in the instance of sampling devices 60, 60A, 60B, 60C may be applied to each of the other embodiments in certain variations. For example, the waste liquid channel 138 may be provided in the sample introduction channel 130 as described in the instance of sampling device 60 may be applied to one or each of the sampling devices 60A, 60B, and 60C.

In at least one example embodiment, of the present disclosure a sampling method for moving a liquid sample from a cell culturing unit (e.g., culturing device 11) to a sampling unit (e.g., sampling device 60, 60A to 60C) is provided. the sampling unit may include a sampling channel 64 through which the sample may flow, a detection unit 75 provided in the sampling channel 64 so as to come in contact with the sample, and a sample introduction channel 130 that connects the culturing unit and the sampling channel 64 upstream of the detection unit 75. The culturing unit and/or the sample introduction channel 130 may include an aseptic filter 58, 136 in a section up to a portion where the sample is introduced into the sampling channel 64. The sampling method may include a sampling step and an adhering substance removal step. The sampling step may include introducing the sample from the culturing unit to the sampling channel 64 through the sample introduction channel 130 and detecting the sample by the detection unit 75. The adhering substance removal step may include removing an adhering substance that is adhered to the aseptic filter 58, 136, for example in the sampling step, by allowing a fluid to flow from the sampling channel 64 to the sample introduction channel 130.

The sampling method may enable removal of the adhering substance adhering to the aseptic filter 58, 136, for example, due to the execution of the sampling step, by allowing a fluid to flow from the sampling channel 64 side during the adhering substance removal step. As a result, clogging of the aseptic filter 58, 136 due to the adhering substance may be reduced. The sampling method may thus enable satisfactory collection of the sample via the aseptic filter 58, 136 with the aseptic state on the culturing unit (e.g., culturing device 11) side being maintained by the aseptic filter 58, 136.

The sampling step may include allowing the sample to flow from the culturing unit (e.g., culturing device 11) and into the sampling channel 64 through the sample introduction channel 130 at a plurality of flow rates. Thus, it may be possible to enhance the effect of washing away aggregates captured on the filter surface on the sampling channel side and to reduce excessive capture of the aggregates on the filter surface on the culturing unit side.

The sampling step may include changing the plurality of flow rates of the sample stepwise from a high flow rate to a low flow rate. As a result, at the start of sampling, aggregates captured on the filter surface on the sampling channel side may be washed away by the sample at the high flow rate and the sample may be stably collected and detected at the low flow rate which is set later.

The high flow rate (i.e., first flow rate) may be set to be three to ten times the low flow rate (i.e., second flow rate). With this configuration, the sampling method may achieve a smoother transmission of the aggregates through the aseptic filter 58, 136.

The sampling unit (e.g., sampling device 60, 60A, 60B, and/or 60C) may include a cleaning solution storage unit 70 connected to an upstream side of the sampling channel 64 and configured to store a cleaning solution. The adhering substance removal step may include allowing the cleaning solution to flow into the sample introduction channel 130 through the sampling channel 64 as the fluid. With this configuration, the sampling method may enable removal of the adhering substance on the aseptic filter 58, 136 using the cleaning solution.

A cleaning step for cleaning the detection unit 75 may include supplying the cleaning solution from the cleaning solution storage unit 70 to the detection unit 75 through the sampling channel 64, which may be performed at a timing different from a timing at which the adhering substance removal step is performed. With this configuration, the sampling method may enable execution of the adhering substance removal step at an appropriate timing.

The sample introduction channel 130 may include a pressure sensor 146 that is configured to detect a pressure in the sample introduction channel 130 and/or a bubble sensor 148 that is configured to detect a bubble in the sample introduction channel 130. The adhering substance removal step may be performed based on that, in the sampling step, a pressure detected by the pressure sensor 146 is equal to or higher than a pressure threshold value and/or a number of bubbles detected by the bubble sensor 148 is equal to or greater than a prescribed value. With this configuration, the sampling method may enable detection of a degree of clogging of the aseptic filter 58, 136 with high accuracy and enable execution of the adhering substance removal step as needed.

A waste liquid channel 138 may include a channel that is different from the culturing unit that may be connected to the sample introduction channel 130 between the culturing unit (e.g., culturing device 11) and the aseptic filter 136. The adhering substance removal step may include guiding the fluid that has passed through the aseptic filter 136 to the waste liquid channel 138. With this configuration, even if the cleaning solution is supplied into the sample introduction channel 130 in order to remove the adhering substance on the aseptic filter 136, the inflow of the cleaning solution into the culturing device 11 may be prevented by discharging the cleaning solution through the waste liquid channel 138.

The sampling channel 64 may include a first pump (e.g., main-mechanism-side pump 92) that allows the cleaning solution to flow from the cleaning solution storage unit 70 to the sampling channel 64 and/or a bypass channel 150 that bypasses the first pump. The sample introduction channel 130 may include a second pump (e.g., introduction pump 142) that may be rotated in a first direction for introducing the sample into the sampling channel 64 and/or a second direction for sending the fluid toward the culturing unit (e.g., culturing device 11). The cleaning solution may be supplied to the detection unit 75 by rotating the first pump and interrupting the bypass channel 150. The adhering substance removal step may include stopping the rotation of the first pump and rotating the second pump in the second direction to allow the cleaning solution to flow into the sample introduction channel 130 through the bypass channel 150. With this configuration, the sampling method may enable easy switching between the cleaning step and the adhering substance removal step.

A cleaning step for cleaning the detection unit 75 by supplying the cleaning solution from the cleaning solution storage unit 70 to the detection unit 75 through the sampling channel 64 may be performed simultaneously with the adhering substance removal step. Thus, with the sampling method, cleaning of the detection unit 75 with the cleaning solution and removal of the adhering substance adhering to the aseptic filter 58 may be efficiently performed.

An amount of the cleaning solution flowing through the sample introduction channel 130 during the adhering substance removal step may be set to be less than an amount of the cleaning solution flowing through the detection unit 75 during the cleaning step. With this configuration, the sampling method may enable removal of the adhering substance on the aseptic filter 58 while stably cleaning the detection unit 75.

The sampling unit (e.g., sampling device 60C) may include an air port 160 connected to the sampling channel 64 on a downstream side of the detection unit 75 that is capable of taking air into the sampling channel 64. The adhering substance removal step may include allowing the sample in the sampling channel 64 to flow into the sample introduction channel 130 by air taken from the air port 160 to remove the adhering substance by the sample. The sampling method may also enables removal of the adhering substance on the aseptic filter 58 by allowing the sample to flow back by the inflow of air.

The invention claimed is:

1. A sampling method for using a sampling unit with a cell culturing unit, the method comprising:

moving a sample from the cell culturing unit to the sampling unit via a sample introduction channel that connects the sampling unit and the cell culturing unit, the sampling unit including a cleaning solution storage unit configured to store a cleaning solution, a sampling channel, and a detection unit disposed in the sampling channel, the moving including causing the sample to move to and into the sampling channel and pass the detection unit; and removing a substance adhered to an aseptic filter that is disposed in a sample introduction channel, the removing including allowing a fluid including the cleaning solution to flow from the sampling unit to and into the sample introduction channel and through the aseptic filter, the sampling unit further including a first pump that is configured to allow the cleaning solution to flow from the cleaning solution storage unit to the sampling channel, to a bypass channel that bypasses the first pump, or to the sampling channel and the bypass channel, the cleaning solution being able to be supplied to the detection unit by rotation the first pump and interrupting the bypass channel, the sample introduction channel further including a second pump that is rotatable in a first direction for introducing the sample to and into the sampling unit and a second direction for sending the fluid toward the cell culturing unit, the removing including stopping the rotation of the first pump and rotating the second pump in the second direction to allow the cleaning solution to flow to and into the sample introduction channel through the bypass channel.

2. The sampling method of claim 1, wherein the moving includes allowing the sample to flow from the cell culturing unit to and into the sampling introduction channel at a plurality of flow rates.

3. The sampling method of claim 2, wherein the moving includes changing the plurality of flow rates from a first flow rate to a second flow rate, the first flow rate being greater than the second flow rate.

4. The sampling method of claim 3, wherein the first flow rate is three times to ten times greater than the second flow rate.

5. The sampling method of claim 1, wherein the sampling method further includes:

cleaning the detection unit by supplying the cleaning solution from the cleaning solution storage unit to the detection unit through the sampling channel.

6. The sampling method of claim 5, wherein the cleaning of the detection unit is performed at a first timing different from a second timing of the removing of the substance adhered to the aseptic filter.

7. The sampling method of claim 5, wherein the cleaning of the detection unit is performed concurrently with the removing.

8. The sampling method of claim 1, wherein an amount of the cleaning solution flowing to and into the sample introduction channel during the removing is less than an amount of the cleaning solution supplied to the detection unit.

9. The sampling method of claim 1, wherein the sampling unit includes an air port connected to the sampling channel downstream of the detection unit, the air port configured to allow air into the sampling channel, and the removing includes allowing the sample in the sampling channel to flow to and into the sample introduction channel by air taken from the air port.

10. The sampling method of claim 1, wherein the sample introduction channel includes at least one of a pressure sensor that is configured to detect a pressure in the sample introduction channel and a bubble sensor that is configured to detect a bubble in the sample introduction channel, and the removing occurs when the pressure detected by the pressure sensor is equal to or higher than a predetermined pressure threshold value and/or a number of bubbles detected by the bubble sensor is equal to or greater than a predetermined bubble threshold value.

11. The sampling method of claim 1, wherein a waste liquid channel is connected to the sample introduction channel between the cell culturing unit and the aseptic filter, and the removing further includes guiding the fluid that has passed through the aseptic filter to the waste liquid channel.

12. A sampling method for using a sampling unit with a cell culturing unit, the method comprising:

moving a sample from the cell culturing unit to the sampling unit via a sample introduction channel that connects the sampling unit and the cell culturing unit and includes an aseptic filter, the sampling unit including a sampling channel and a detection unit disposed in the sampling channel, the moving including causing the sample to move to and into the sampling channel pass the detection unit; and allowing a cleaning solution to flow from a cleaning solution storage unit of the sampling unit to and into the sampling introduction channel and through the aseptic filter to remove a substance from the aseptic filter as disposed during the moving of the sample from the cell culturing unit to the sampling unit, the sampling unit further including a first pump that is configured to allow the cleaning solution to flow from the cleaning solution storage unit to the sampling channel, to a bypass channel that bypasses the first pump, or to the sampling channel and the bypass channel, the cleaning solution being able to be supplied to the detection unit by rotation the first pump and interrupting the bypass channel, the sample introduction channel further including a second pump that is rotatable in a first direction for introducing the sample to and into the sampling unit and a second direction for sending the cleaning solution toward the cell culturing unit, the allowing including stopping the rotation of the first pump and rotating the second pump in the second direction to allow the cleaning solution to flow to and into the sample introduction channel through the bypass channel.

13. The sampling method of claim 12, wherein the sample introduction channel includes at least one of a pressure sensor that is configured to detect a pressure in the sample introduction channel and a bubble sensor that is configured to detect a bubble in the sample introduction channel, and the allowing occurs when the pressure detected by the pressure sensor is equal to or higher than a predetermined pressure threshold value and/or a number of bubbles detected by the bubble sensor is equal to or greater than a predetermined bubble threshold value.

14. A sampling unit configured to receive a sample from a cell culturing unit, the sampling unit comprising:

a sample introduction channel that connects the sampling unit and the cell culturing unit that allows the sample to be received by the sampling unit and that includes an aseptic filter;

a sampling channel that includes a detection unit and configured to receive the sample from the sample introduction channel; and a cleaning solution storage unit configured to store a cleaning solution and fluidically connected to the sampling channel such that the cleaning solution can be moved from the cleaning solution storage unit to the sampling channel, the sampling channel including a first pump that is configured to allow the cleaning solution to flow from the cleaning solution storage unit to the sampling channel and a bypass channel that bypasses the first pump, the sample introduction channel further including a second pump that is rotatable in a first direction for introducing the sample to and into the sampling channel and a second direction for sending the cleaning solution toward the cell culturing unit, and removal of a substance adhered to the aseptic filter including stopping rotation of the first pump and rotating the second pump in the second direction to allow the cleaning solution to flow to and into the sample introduction channel through the bypass channel.

15. The sampling unit of claim 14, wherein the sampling unit includes an air port connected to the sampling channel downstream of the detection unit, the air port configured to allow air into the sampling channel, and the removing of the substance adhered to the aseptic filter includes allowing the sample in the sampling channel to flow to and into the sample introduction channel by air taken from the air port.

* * * * *